(12) United States Patent
Ketelaars et al.

(10) Patent No.: US 11,957,883 B2
(45) Date of Patent: Apr. 16, 2024

(54) PLUNGER ROD AND SYRINGE ASSEMBLY SYSTEM AND METHOD

(71) Applicant: AMGEN INC., Thousand Oaks, CA (US)

(72) Inventors: Jeroen Ketelaars, Breda (NL); Lawrence G. Leka, Santa Barbara, CA (US); Ernesto J. Perez, San Juan, PR (US); Manuel Rey, San Juan, PR (US); Jomasoel Rivera, Caguas, PR (US); Javier O. Tapia, Gurabo, PR (US); Martin van Wezel, Breda (NL); Francisco Almedina Vazquez, Cayey, PR (US); Noel Wah Reyes, Canovanas, PR (US)

(73) Assignee: AMGEN INC., Thousand Oaks, CA (US)

(*) Notice: Subject to any disclaimer, the term of this patent is extended or adjusted under 35 U.S.C. 154(b) by 1118 days.

(21) Appl. No.: 16/488,172

(22) PCT Filed: Mar. 20, 2018

(86) PCT No.: PCT/US2018/023306
§ 371 (c)(1),
(2) Date: Aug. 22, 2019

(87) PCT Pub. No.: WO2018/183039
PCT Pub. Date: Oct. 4, 2018

(65) Prior Publication Data
US 2021/0283337 A1    Sep. 16, 2021

Related U.S. Application Data

(60) Provisional application No. 62/477,521, filed on Mar. 28, 2017.

(51) Int. Cl.
*B23P 21/00* (2006.01)
*A61M 5/315* (2006.01)
*B23P 19/04* (2006.01)

(52) U.S. Cl.
CPC ......... *A61M 5/31515* (2013.01); *B23P 21/00* (2013.01); *A61M 2207/10* (2013.01); *B23P 19/047* (2013.01)

(58) Field of Classification Search
CPC .......... A61M 5/31515; A61M 2207/10; A61M 5/178; A61M 5/008; A61M 5/24; B23P 19/047; B65B 3/006; B65B 7/2821
See application file for complete search history.

(56) References Cited

U.S. PATENT DOCUMENTS 2,684,556 A    7/1954  Mollinari
2,756,606 A *  7/1956  Staples .................... B23Q 5/56
                                                      74/89.32

(Continued)

FOREIGN PATENT DOCUMENTS

CA    3055511 A1    3/2013
CN    102554613 A   7/2012

(Continued)

OTHER PUBLICATIONS

Chinese Patent Application No. 201880020386.9, First Office Action, dated May 24, 2021.

(Continued)

*Primary Examiner* — Lawrence Averick
(74) *Attorney, Agent, or Firm* — MARSHALL, GERSTEIN & BORUN LLP

(57) ABSTRACT

A machine for coupling a plunger rod to a syringe assembly may include a carriage including a cradle having a seat portion sized to receive a syringe assembly and an aperture portion disposed above the seat portion and sized to receive (Continued)

a plunger rod. An actuating device may be operatively coupled to the carriage and adapted to move the cradle from a first position to a second position to couple the plunger rod to the syringe assembly. The carriage may be selected from separate and interchangeable first and second carriages, wherein the first carriage includes a cradle adapted to receive a syringe assembly of a first size and the second carriage including a cradle sized to receive a syringe assembly of a second size that is different from the first size.

16 Claims, 11 Drawing Sheets

(56) References Cited

U.S. PATENT DOCUMENTS

| | | | |
|---|---|---|---|
| 2,765,606 A | 10/1956 | Brown | |
| 2,823,500 A * | 2/1958 | Brown | B65B 3/006 53/328 |
| 2,998,050 A | 8/1961 | Hamilton et al. | |
| 3,503,113 A * | 3/1970 | Lagsdin | A61M 5/00 29/777 |
| 3,588,985 A | 6/1971 | Shields | |
| 3,623,210 A | 11/1971 | Shields | |
| 3,683,483 A * | 8/1972 | Klettke | B65B 3/006 29/785 |
| 3,708,942 A * | 1/1973 | Leonard | F16B 15/0046 52/693 |
| 3,708,945 A | 1/1973 | Klettke | |
| 3,807,119 A * | 4/1974 | Shields | B65B 7/2821 29/777 |
| 4,003,123 A | 1/1977 | Duke | |
| 4,046,616 A | 9/1977 | Klein | |
| 6,742,246 B2 * | 6/2004 | Stroup | B23P 19/04 198/612 |
| 6,915,619 B2 * | 7/2005 | Baldwin | B65B 9/02 53/399 |
| 8,479,365 B2 * | 7/2013 | Tubota | B23P 19/02 141/147 |
| 2003/0135978 A1 * | 7/2003 | Stroup | B23P 21/00 29/559 |
| 2004/0088951 A1 | 5/2004 | Baldwin et al. | |
| 2004/0168741 A1 * | 9/2004 | Baldwin | B65B 3/003 141/98 |
| 2012/0000046 A1 * | 1/2012 | Tubota | B65B 7/2821 29/240 |
| 2016/0038689 A1 | 2/2016 | Lee et al. | |

FOREIGN PATENT DOCUMENTS

| | | |
|---|---|---|
| CN | 103249442 A | 8/2013 |
| CN | 103707056 A | 4/2014 |
| JP | 2013-153849 A | 8/2013 |
| KR | 20030004280 A | 1/2003 |
| WO | WO-2012045833 A1 | 4/2012 |

OTHER PUBLICATIONS

Japanese Patent Application No. 2019-553192, Notice of Rejection, dated Dec. 7, 2021.
International Search Report for International Application No. PCT/US2018/023306, dated Aug. 13, 2018.
Written Opinion for International Application No. PCT/US2018/023306, dated Aug. 13, 2018.
Eurasian Application No. 202190785, Office Action and Search Report, dated Sep. 8, 2021.
Chile Patent Application No. 201902710, Office Action and Search Report, dated Jul. 13, 2020.
Chilean Patent Application No. 202100094, Office Action, dated May 19, 2022.
Chinese Patent Application No. 202210192951.8, Office Action, dated Nov. 24, 2023.
Canadian Patent Application No. 3,052,676, Office Action, dated Jan. 4, 2024.

* cited by examiner

PLUNGER ROD AND SYRINGE ASSEMBLY SYSTEM AND METHOD

CROSS-REFERENCE TO RELATED APPLICATION

This is the United States National Phase of PCT/US18/23306, filed Mar. 20, 2018, which claims the priority benefit of U.S. Provisional Patent Application No. 62/477,521, filed Mar. 28, 2017, the entire contents of each of which are hereby incorporated herein by reference.

FIELD OF THE DISCLOSURE

The present disclosure generally relates to medicinal syringes and, more particularly, to mechanisms and methods for coupling a plunger rod to a syringe assembly of a medicinal syringe.

BACKGROUND

A typical medicinal syringe includes a syringe assembly containing a fluid such as a medicament or drug product and a plunger rod coupled to the syringe assembly. The plunger rod may be coupled to a plunger disposed within a syringe barrel of the syringe assembly after the syringe is filled with fluid. The plunger may include internal threads that are sized to couple to external threads of a distal end of the plunger rod. When the distal end of the plunger rod is threaded to the plunger, the plunger rod is coupled to the syringe assembly. A force applied to the plunger rod can then drive the plunger through the syringe barrel to dispense the fluid contained within the syringe. The plunger rod includes a proximal rod end having a flange, which an operator may press with the operators thumb while gripping the syringe barrel between two fingers. Syringe assemblies are sized to hold different quantities of fluid, and plunger rods may also be sized to match their syringe assembly counterpart. When coupling a plunger rod to a plunger, care must be taken to avoid applying excessive pressure that may prematurely expel fluid and/or compromise the Container Closure Integrity of the sealed prefilled syringe. In the prefilled syringe, the fill level of the fluid contained within the syringe barrel may differ within a batch of prefilled syringes, and thus the position of a plunger within a syringe barrel can also differ within the batch. As such, existing systems that couple plunger rods to prefilled syringes must be adaptable to accommodate for variations in fill level to prevent premature expulsion of the fluid.

A typical machine used for coupling plunger rods and syringe assemblies is fully automated and designed to perform a number of process steps, including loading the plunger rods and syringe assemblies to the machine, operating the machine, coupling the plunger rod to the plunger, and unloading the finished product from the machine. Fully automated technology is particularly useful for preparing large batches of 2000 or more coupled plunger rod and syringe assemblies. To adjust the fully automated machine for assembling plunger rods and syringe assemblies of a different size, referred herein as the "changeover process," the machine must be partially disassembled, adjusted, and/or reassembled before operating. This changeover process often requires a skilled operator to manage the many components involved in the disassembly, adjustment and tooling, and reassembly of the machine, which can be a very time-intensive procedure. Moreover, the known machine has a large footprint and is generally non-portable once the machine is established in a processing laboratory. Using such a large-batch machine can be impractical for assembling small batches and easily assembly of syringe assemblies of different sizes.

SUMMARY

In accordance with a first exemplary aspect, a machine for coupling a plunger rod to a syringe assembly may include a selected carriage including a cradle having a seat portion sized to receive a syringe assembly and an aperture portion disposed above the seat portion and sized to receive a plunger rod. An actuating device may be operatively coupled to the selected carriage and adapted to move the cradle from a first position to a second position to couple the plunger rod to the syringe assembly. The selected carriage may be selected from separate and interchangeable first and second carriages, wherein the first carriage includes a cradle adapted to receive a syringe assembly of a first size and the second carriage including a cradle sized to receive a syringe assembly of a second size that is different from the first size.

In accordance with a second exemplary aspect, a method of using a machine to couple a plunger rod to a syringe assembly may include decoupling a second carriage from an actuating device and coupling a first carriage to the actuating device after decoupling the second carriage from actuating device, the first carriage including a movable first cradle adapted to receive a syringe assembly of a first size. Next, the method may include positioning a first syringe assembly onto the movable first cradle of the first carriage, the first syringe assembly including a distal end and a proximal end, a syringe barrel, and a plunger disposed within the syringe barrel. Then, the method may include positioning a first plunger rod onto the first cradle of the first carriage, the first plunger rod including a distal rod end and a proximal rod end and wherein the distal rod end is disposed above the proximal end of the first syringe assembly and is axially aligned with the plunger. Further, the method may include activating the actuating device coupled to the first carriage to move the first cradle from a first position to a second position, thereby applying a force to the first plunger rod causing the first plunger rod to become coupled to the first syringe assembly.

In accordance with a third exemplary aspect, a machine for coupling a plunger rod to a syringe assembly may include a carriage having a movable cradle including a seat portion sized to receive a syringe assembly and an aperture portion disposed above the seat portion sized to receive a plunger rod. An actuating device may be operatively coupled to the carriage and adapted to move the cradle from a first position to a second position to couple the plunger rod to the syringe assembly. The machine may further include an elongated pressure plate positioned adjacent to the carriage and defining an inlet and an outlet, the inlet being sized to receive a proximal end of the plunger rod and apply a downward force on the proximal end of the plunger rod as the plunger rod moves from the inlet to the outlet. A constant tension spring may be coupled to the pressure plate, the constant tension spring providing a downward force to the pressure plate such that the downward force is transferred to the plunger rod via the pressure plate as the cradle moves between the first position and the second position.

In accordance with a fourth exemplary aspect, a machine for coupling a plunger rod to a syringe assembly may include a carriage having a movable cradle including a seat portion sized to receive a syringe assembly and an aperture portion disposed above the seat portion sized to receive a plunger rod. The machine may include an actuating device operatively coupled to the carriage and adapted to move the cradle from a first position to a second position to couple the plunger rod to the syringe assembly. A pressure plate may be positioned adjacent to the carriage so that the cradle moves beneath the pressure plate when the cradle moves from the first position to the second position, the pressure plate adapted to apply a downward force to the plunger rod disposed in the aperture portion of the cradle when the cradle moves from the first position to the second position. The actuating device may include a lever operatively coupled to the carriage and adapted to be manipulated to index the cradle from the first position to the second position.

In accordance with a fifth exemplary aspect, a machine for coupling a plunger rod to a syringe assembly may include a carriage having a movable cradle including a seat portion sized to receive a syringe assembly and an aperture portion disposed above the seat portion sized to receive a plunger rod. An actuating device may be operatively coupled to the carriage and adapted to index the cradle from a first position to a second position only once upon an activation event for coupling the plunger rod to the syringe assembly.

In accordance with a sixth exemplary aspect, a method of using a machine to couple a plunger rod to a syringe assembly may include positioning a syringe assembly onto a movable cradle of a carriage, wherein the syringe assembly includes a distal end and a proximal end, a syringe barrel, and a plunger disposed within the syringe barrel at the proximal end of the syringe assembly. Next, the method may include positioning a plunger rod onto the cradle where the plunger rod may include a distal rod end and a proximal rod end and wherein the distal rod end of the plunger rod is disposed above the proximal end of the syringe assembly and is axially aligned with the plunger. The method may include activating an actuating device operatively connected to the carriage. Further, the method may include indexing the cradle from the first position to the second position only once in response to activating the actuating device, wherein a force may be applied to either or both of the syringe assembly and the plunger rod as the cradle indexes from the first position to the second position to couple the plunger rod to a plunger of the syringe assembly.

In accordance with a seventh exemplary aspect, a machine for coupling a plunger rod to a syringe assembly may include a carriage having a movable cradle including a seat portion sized to receive a syringe assembly and an aperture portion disposed above the seat portion sized to receive a plunger rod. An actuating device may be operatively coupled to the carriage and adapted to move the cradle from a first position to a second position to couple the plunger rod to the syringe assembly. Further, a friction element may be disposed adjacent to the carriage and below the pressure plate where the friction element may be adapted to engage a syringe barrel of the syringe assembly carried by the cradle as the cradle moves from the first position to the second position, thereby applying a rotational force to the syringe assembly and spin the syringe assembly relative to the plunger rod when the cradle moves from the first position to the second position In accordance with an eighth exemplary aspect, a method of using a machine to couple a plunger rod to a syringe assembly may include positioning a syringe assembly onto a movable cradle of a carriage, wherein the syringe assembly includes a distal end and a proximal end, a syringe barrel, and a plunger disposed within the syringe barrel at the proximal end of the syringe assembly. The method may include positioning a plunger rod onto the cradle, the plunger rod including a distal rod end and a proximal rod end and wherein the distal rod end of the plunger rod is disposed above the proximal end of the syringe assembly and is axially aligned with the plunger. Then, the method may include activating an actuating device operatively connected to the carriage to move the cradle from a first position to a second position, and rotating the syringe assembly relative to the plunger rod when the cradle moves between the first position and the second position, thereby causing a first threaded portion on the distal rod end of the plunger rod to become threadably coupled to a second threaded portion of the plunger of the syringe assembly.

In accordance with a ninth exemplary aspect, a machine for coupling a plunger rod to a syringe assembly may include a carriage having a movable cradle including a seat portion sized to receive a syringe assembly and an aperture portion disposed above the seat portion sized to receive a plunger rod. The machine may include an actuating device operatively coupled to the carriage and adapted to index the cradle from a first position to a second position only once upon an activation event to couple the plunger rod to the syringe assembly. A pressure plate may be positioned adjacent to the carriage so that the cradle moves beneath the pressure plate when the cradle moves from the first position to the second position, the pressure plate adapted to apply a downward force to the plunger rod disposed in the aperture portion of the cradle when the cradle moves from the first position to the second position. The actuating device may include a servomotor and an operation switch for operatively controlling the servomotor, the servomotor coupled to the carriage to index the cradle via the carriage.

In accordance with a tenth exemplary aspect, a machine for coupling a plunger rod to a syringe assembly may include a base and a carriage attached to the base and movable relative to the base, the carriage including a movable cradle having a seat portion sized to receive a syringe assembly and an aperture portion disposed above the seat portion sized to receive a plunger rod. An actuating device may be coupled to the carriage and adapted to index the cradle from a first position to a second position. The machine may include a pressure plate supported by the base and positioned adjacent to the carriage so that the cradle moves beneath the pressure plate when the cradle moves from the first position to the second position, the pressure plate adapted to apply a downward force to the plunger rod disposed in the aperture portion of the cradle. The cradle may include a cradle axis that is coaxial with longitudinal axes of the syringe assembly and plunger rod when the syringe assembly and plunger rod are disposed in the cradle, the cradle axis being disposed at an angle greater than zero degrees relative to vertical.

In accordance with an eleventh exemplary aspect, a machine for coupling a plunger rod to a syringe assembly may include a carriage having a movable cradle including a seat portion sized to receive a syringe assembly and an aperture portion disposed above the seat portion sized to receive a plunger rod, an actuating device operatively coupled to the carriage and adapted to move the cradle from a first position to a second position to couple the plunger rod to the syringe assembly, and a pressure plate positioned adjacent to the carriage so that the cradle moves beneath the pressure plate when the cradle moves from the first position to the second position, the pressure plate adapted to apply a downward force to the plunger rod disposed in the aperture portion of the cradle when the cradle moves from the first position to the second position. The machine may include at least one of the following (a) through (e) aspects. In aspect (a), a constant tension spring may be operatively coupled to the pressure plate and the pressure plate may define an inlet portion adapted to receive a proximal end of the plunger rod when the cradle moves from the first position to the second position. The constant tension spring may provide the downward force to the plunger rod, applied via the pressure plate, when the cradle moves between the first position and the second position. In aspect (b), a friction element may be disposed adjacent to the carriage and below the pressure plate. The friction element may be adapted to engage a syringe barrel of the syringe assembly carried by the cradle as the cradle moves from the first position to the second position. The friction element may be adapted to apply a rotational force to the syringe barrel to spin the syringe assembly relative to the plunger rod when the cradle moves from the first position to the second position. In aspect(c), the actuating device may be operatively connected to the carriage and adapted to index the cradle between the first position and the second position in response to an activation event. In aspect (d), the cradle may include a cradle axis that is coaxial with longitudinal axes of the syringe assembly and plunger rod when the syringe assembly and plunger rod are disposed in the cradle. The cradle axis may be disposed at an angle greater than zero degrees relative to vertical. Finally in aspect (e), the carriage may be selected from separate and interchangeable first and second carriages. The first carriage may include a cradle having a seat portion sized to receive a syringe assembly of a first size and the second carriage may include a cradle having a seat portion sized to receive a syringe assembly of a second size.

In accordance with a twelfth exemplary aspect, a method of using a machine to couple a plunger rod to a syringe assembly may include positioning a syringe assembly onto a movable cradle of a carriage, wherein the syringe assembly includes a distal end and a proximal end, a syringe barrel, and a plunger disposed within the syringe barrel at the proximal end of the syringe assembly. Next, the method may include positioning a plunger rod onto the cradle where the plunger rod may include a distal rod end and a proximal rod end and wherein the distal rod end of the plunger rod is disposed above the proximal end of the syringe assembly and is axially aligned with the plunger. The method may include activating an actuating device operatively connected to the carriage. Further, the method may include indexing the cradle from the first position to the second position more than once in response to activating the actuating device, wherein a force may be applied to either or both of the syringe assembly and the plunger rod as the cradle indexes from the first position to the second position to couple the plunger rod to a plunger of the syringe assembly.

In further accordance with any one or more of the foregoing first through twelfth aspects and methods, the machine for coupling a plunger rod and syringe assembly and method for using the machine may include any one or more of the following forms or method steps.

In a preferred form, the machine may include a selected pressure plate positioned above the cradle so that the cradle moves beneath the selected pressure plate when the cradle moves from the first position to the second position. The selected pressure plate may be adapted to apply a downward force to the plunger rod disposed in the aperture portion of the cradle when the cradle moves from the first position to the second position.

In a preferred form of the machine, the first carriage may include a first pressure plate coupled to the first carriage, and the second carriage may include a second pressure plate coupled to the second carriage, such that the selected pressure plate is coupled to the selected carriage.

In a preferred form, the machine may include a quick-change fastener and a table, the selected carriage may be removably coupled to the table by the quick-change fastener.

In a preferred form of the machine, the first carriage may include a first base and the second carriage may include a second base, and the actuating device may include a servomotor adapted to be operatively connected to the first and second bases.

In a preferred form, the machine may include a selected friction element disposed adjacent to the selected carriage. The selected friction element may be adapted to engage a syringe barrel of the syringe assembly carried by the cradle as the cradle moves from the first position to the second position. The friction element may be adapted to apply a rotational force to the syringe barrel to spin the syringe assembly relative to the plunger rod when the cradle moves from the first position to the second position.

In a preferred form of the machine, the first carriage may include a first guide plate coupled to the first carriage and carrying a first friction element and the second carriage may include a second guide plate coupled to the second carriage and carrying a second friction element such that the selected friction element is carried by a selected guide plate coupled to the selected carriage.

In a preferred form, the machine may include a selected constant tension spring operatively coupled to the selected pressure plate. The selected pressure plate defining an inlet portion may be adapted to receive a proximal end of the plunger rod when the cradle moves from the first position to the second position. The selected constant tension spring may provide the downward force to the plunger rod, applied via the selected pressure plate, when the cradle moves between the first position and the second position.

In a preferred form, the machine may include a servomotor and an operation switch for operatively controlling the servomotor, the servomotor coupled to the carriage to move the cradle via the carriage.

In a preferred form of the machine, the inlet may include a ramped surface positioned above the outlet relative to the carriage.

In a preferred form, the machine may include at least one guide post, the pressure plate slidably coupled to the at least one guide post in a direction parallel to a longitudinal axis of the carriage.

In a preferred form, the machine may include a threaded rod for adjustably mounting the pressure plate relative to the carriage such that the pressure plate is adjustable in the direction parallel to the longitudinal axis of the carriage to accommodate plunger rods at different heights.

In a preferred form, the machine may include a friction element disposed adjacent to the carriage and below the pressure plate. The friction element may be adapted to engage a syringe barrel of the syringe assembly carried by the cradle as the cradle moves from the first position to the second position. The friction element may be adapted to apply a rotational force to the syringe barrel to spin the syringe assembly relative to the plunger rod.

In a preferred form of the machine, the friction element may be immovably fixed relative to the cradle.

In a preferred form, the machine may include a guide plate and the friction element may be fixed to the guide plate.

In a preferred form of the machine, the friction element may be an elongated cord.

In a preferred form of the machine, the friction element may be an elastomeric material.

In a preferred form of the machine, the actuating device may be adapted to index the cradle between the first position and the second position in response to an activation event.

In a preferred form of the machine, the actuating device may index the cradle only once upon an activation event.

In a preferred form of the machine, the actuating device may index the cradle two or more times upon an activation event.

In a preferred form of the machine, the actuating device may include a lever for a user to manually index the cradle from the first position to the second position.

In a preferred form of the machine, the lever may be movably attached to a base of the carriage, and wherein the lever may be arranged to perform the activation event when the lever moves from a resting position to an activated position.

In a preferred form of the machine, the actuating device may include a motor-operated bracket disposed adjacent to the lever, the bracket may be adapted to move the lever between the resting position to the activated position.

In a preferred form of the machine, the actuating device may include a slidable bracket arranged to move the lever.

In a preferred form, the machine may include a pressure plate positioned adjacent to the carriage so that the cradle moves beneath the pressure plate when the cradle moves from the first position to the second position, the pressure plate adapted to apply a downward force to the plunger rod disposed in the aperture portion of the cradle when the cradle moves from the first position to the second position.

In a preferred form, the machine may include a two-hand anti-tie down operation switch arranged to perform the activation event.

In a preferred form of the machine, the actuating device may include a lever operatively coupled to the carriage, the lever arranged to be manually manipulated for performing the activation event.

In a preferred form of the machine, the actuating device may include a lever for a user to manually index the cradle from the first position to the second position.

In a preferred form of the machine, the seat portion of the cradle may include a first roller and a second roller separated by a gap. The first and second rollers of the seat portion may be adapted to engage the syringe barrel of the syringe assembly and retain the syringe barrel in the gap when carried by the cradle, the first and second rollers allowing for the syringe assembly to spin as the cradle indexes from the first position to the second position.

In a preferred form of the machine, each of the first and second rollers may include a rotational axis, the first roller being rotatable about the rotational axis of the first roller and the second roller being rotatable about the rotational axis of the second roller.

In a preferred form of the machine, the servomotor may be programmed to respond to an activation event to move the carriage, the activation event including triggering the operation switch.

In a preferred form of the machine, the servomotor may be programmed to index the cradle more than once in response to the activation event.

In a preferred form of the machine, the servomotor may be adapted to operatively couple to a different carriage.

In a preferred form of the machine, the cradle may include a cradle axis that is coaxial with longitudinal axes of the syringe assembly and plunger rod when the syringe assembly and plunger rod are disposed in the cradle, the cradle axis being disposed at an angle greater than zero degrees relative to vertical.

In a preferred form of the machine, the carriage may include a rotational carousel with a rotational axis that is parallel to the cradle axis such that the rotational axis of the carriage is disposed at an angle greater than zero degrees relative to vertical.

In a preferred form of the machine, the base may include a bottom surface disposed at a first angle relative to horizontal, wherein the longitudinal axis of the cradle is offset from the vertical by the first angle.

In a preferred form, the machine may include a movable plunger rod base coupled to the carriage. The plunger rod base may be disposed above the cradle and may include an orifice sized to receive a flanged proximal end of the plunger rod, the orifice coaxially aligned with the aperture portion of the cradle. The plunger rod base may be movable with the cradle from the first position to the second position.

In a preferred form, the machine may include a holding cap having an outwardly extending tab arranged to extend into the orifice of the plunger rod base, the holding cap removably attached to the plunger rod base. The holding cap may be fixed relative to the carriage and is disposed in the orifice when the cradle is in the first position.

In a preferred form, the machine may include a selected movable plunger rod base coupled to the selected carriage.

In a preferred form of the machine, the plunger rod base may be selected from separate and interchangeable first and second plunger rod bases, the first plunger rod base including an orifice sized to receive a flanged plunger rod end of a first size and the second plunger rod base sized to receive a flanged plunger rod end of a second size that is different from the first size.

In a preferred form of the machine, the carriage may be rotationally disposed relative to the pressure plate.

In a preferred form of the machine, the carriage may include a plurality of cradles carried by the carriage.

In a preferred form, the machine may include an exit chute disposed adjacent to the carriage and at the second position of the cradle. The exit chute may be adapted to receive the plunger rod and syringe assembly from the cradle after the plunger rod is coupled to the syringe assembly.

In a preferred form, the first carriage may include a first exit chute coupled to the first carriage and the second carriage may include a second exit chute coupled to the second carriage such that the selected exit chute is coupled to the selected carriage.

In a preferred form of the machine, the exit chute may include a ramp, the ramp including a slot sized to receive the plunger rod and syringe assembly after the cradle moves to the second position.

In a preferred form, the method may include applying a downward force to the proximal rod end of the first plunger rod when the first cradle moves from the first position toward the second position.

In a preferred form, the method may include indexing the cradle from the first position to the second position two or more times in response to activating the actuating device.

In a preferred form, the method may include fastening the first carriage to a table by a quick-change fastener, wherein the table is connected to the actuating device.

In a preferred form of the method, decoupling the second carriage from the actuating device may include decoupling the quick-change fastener securing the second carriage to the table.

In a preferred form of the method, decoupling the second carriage from the actuating device may include decoupling a servomotor of the actuating device from a receiving member of the second carriage.

In a preferred form of the method, coupling the first carriage to the actuating device may include coupling a servomotor of the actuating device to a receiving member of the first carriage.

In a preferred form, the method may include, prior to decoupling the second carriage from the actuating device, positioning a second syringe assembly onto a second cradle of the second carriage, the second cradle adapted to receive the second syringe assembly of a second size, the second syringe assembly including a distal end and a proximal end, a syringe barrel, and a plunger disposed within the syringe barrel, wherein the second cradle of the second carriage is sized to receive a second syringe barrel of a second size. Further, the preferred form of the method may include positioning a second plunger rod onto the second cradle of the second carriage, the second plunger rod including a distal rod end and a proximal rod end and wherein the distal rod end is disposed above the proximal end of the second syringe assembly and is axially aligned with the plunger. In the preferred form, the method may include activating the actuating device coupled to the second carriage to move the second cradle from a first position to a second position, thereby applying a force to the second plunger rod causing the second plunger rod to become coupled to the second syringe assembly.

In a preferred form of the method, indexing the cradle may include rotating the carriage about a rotational axis of the carriage.

In a preferred form of the method, rotating the carriage may include rotating the carriage greater than zero degrees to index the cradle from the first position to the second position.

In a preferred form of the method, activating the actuating device may include moving a lever, wherein the lever causes the carriage to index the cradle from the first position to the second position.

In a preferred form of the method, activating the actuating device may include triggering an operation switch coupled to a servomotor, wherein the servomotor is arranged to slide a bracket to move the lever.

In a preferred form of the method, activating the actuating device may include triggering an operation switch coupled to a servomotor, wherein the servomotor is operatively coupled to the carriage.

In a preferred form, the method may include applying a downward force to the proximal rod end of the plunger rod when the cradle moves from the first position toward the second position.

In a preferred form of the method, applying a downward force to the proximal rod end of the plunger rod may include moving the plunger rod beneath a pressure plate positioned adjacent to the carriage when the cradle moves from the first position to the second position.

In a preferred form, the method may include applying a rotational force to the syringe barrel of the syringe assembly as the cradle moves from the first position to the second position.

In a preferred form of the method, applying the rotational force may include engaging the syringe assembly with a friction element disposed adjacent to the carriage when the cradle moves from the first position to the second position. The syringe assembly may be rotatable about a longitudinal axis of the cradle.

In a preferred form, the method may include rotating the carriage about a rotational axis of the carriage in a first direction to index the cradle from the first position to the second position.

In a preferred form of the method, rotating the syringe assembly may include rotating the syringe assembly in a direction opposite the first direction of the carriage, wherein the rotational axis of the carriage is parallel to the longitudinal axis of the cradle.

BRIEF DESCRIPTION OF THE DRAWINGS

It is believed that the disclosure will be more fully understood from the following description taken in conjunction with the accompanying drawings. Some of the drawings may have been simplified by the omission of selected elements for the purpose of more clearly showing other elements. Such omissions of elements in some drawings are not necessarily indicative of the presence or absence of particular elements in any of the example embodiments, except as may be explicitly delineated in the corresponding written description. Also, none of the drawings is necessarily to scale.

DETAILED DESCRIPTION OF THE DRAWINGS

Figure 11:
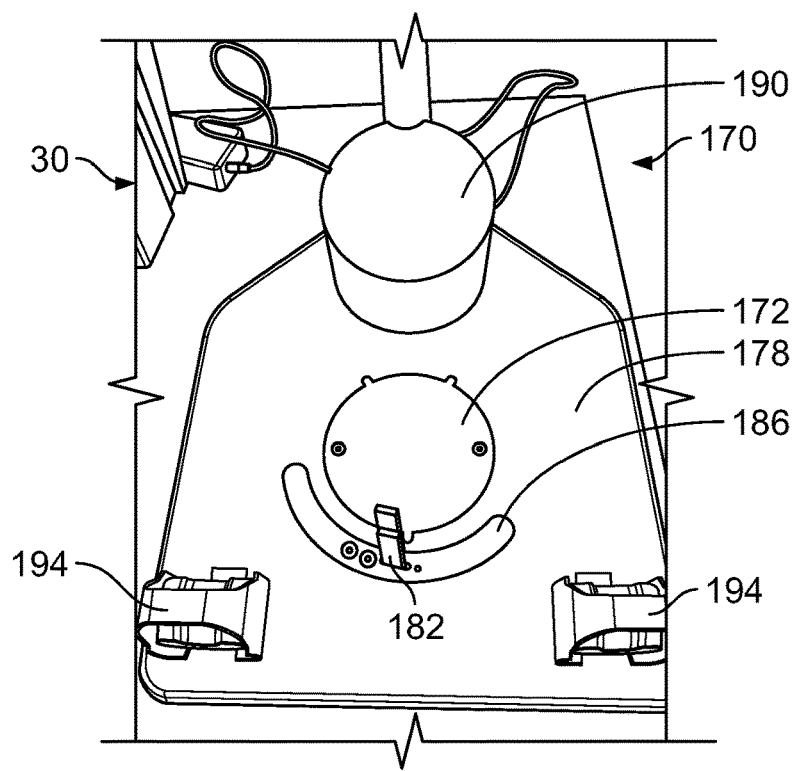
FIG. 11 is a top perspective view of an adaptive actuating system for use with the first example plunger rod assembly machine of FIG. 1.
Figure 12:
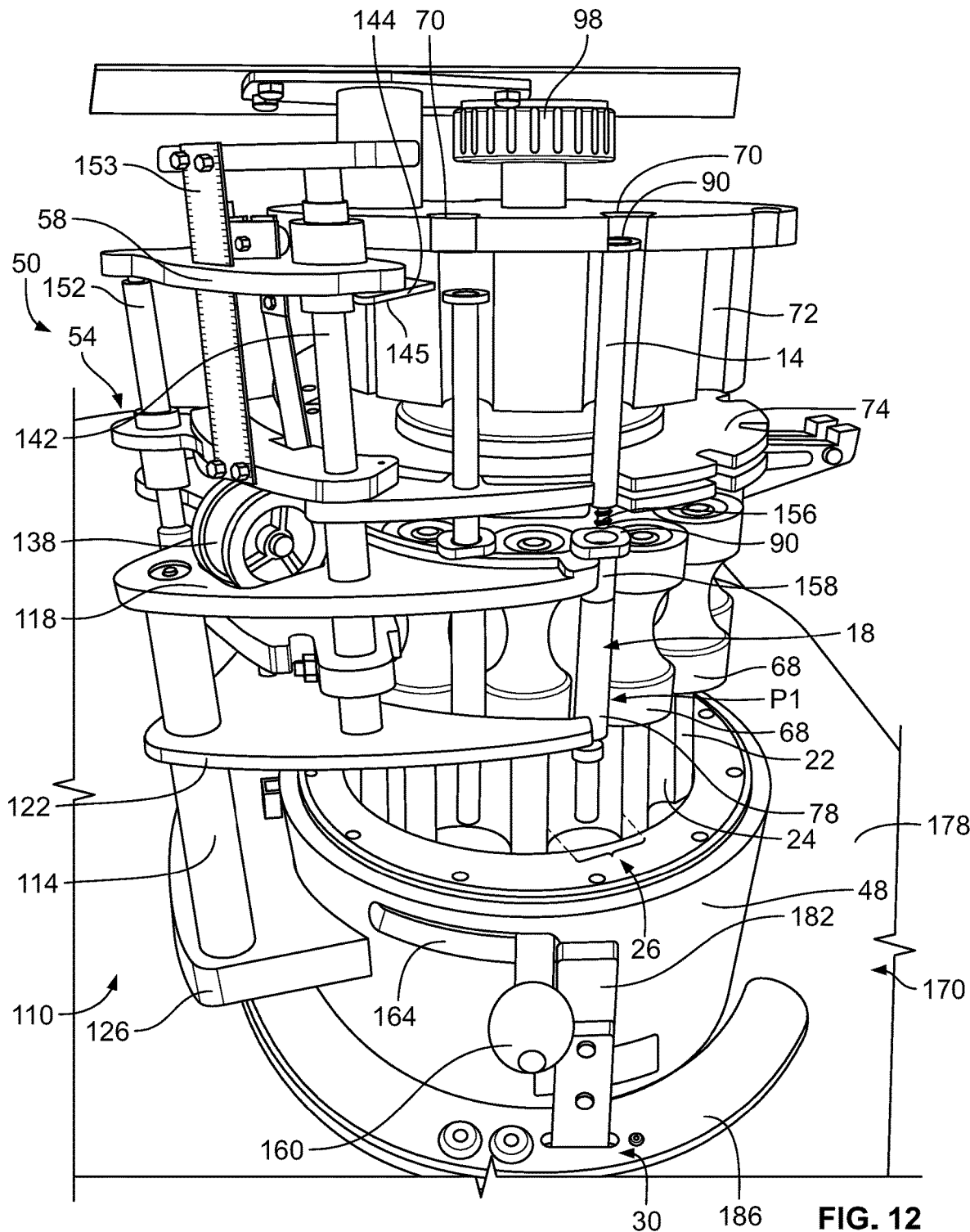
FIG. 12 is a perspective view of a second example plunger rod assembly system including the machine of FIG. 1 coupled to the adaptive actuating system of FIG. 11.
Figure 13:
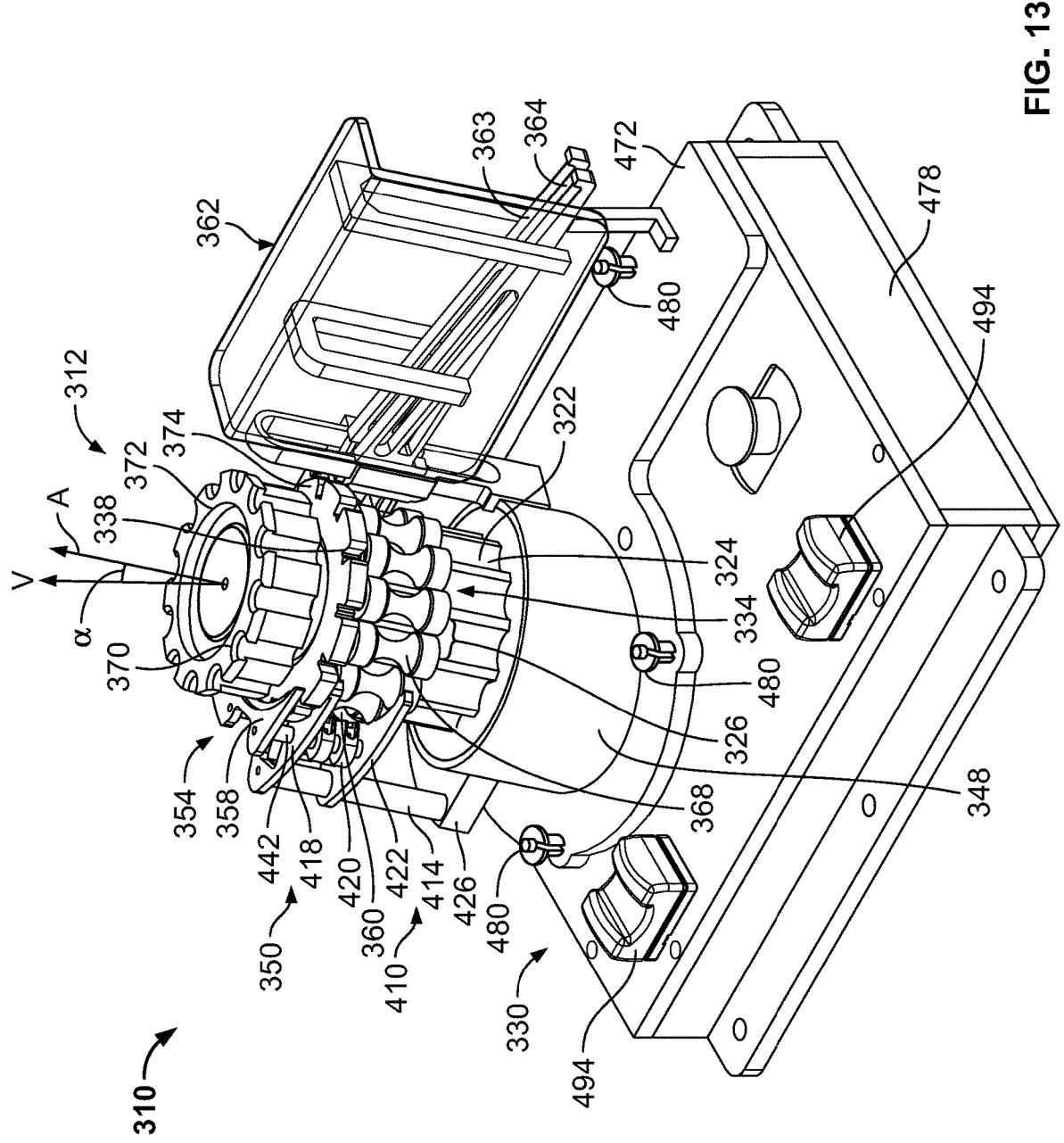
FIG. 13 is a perspective view of a third example plunger rod assembly system in accordance with teachings of the present disclosure.
Figure 14:
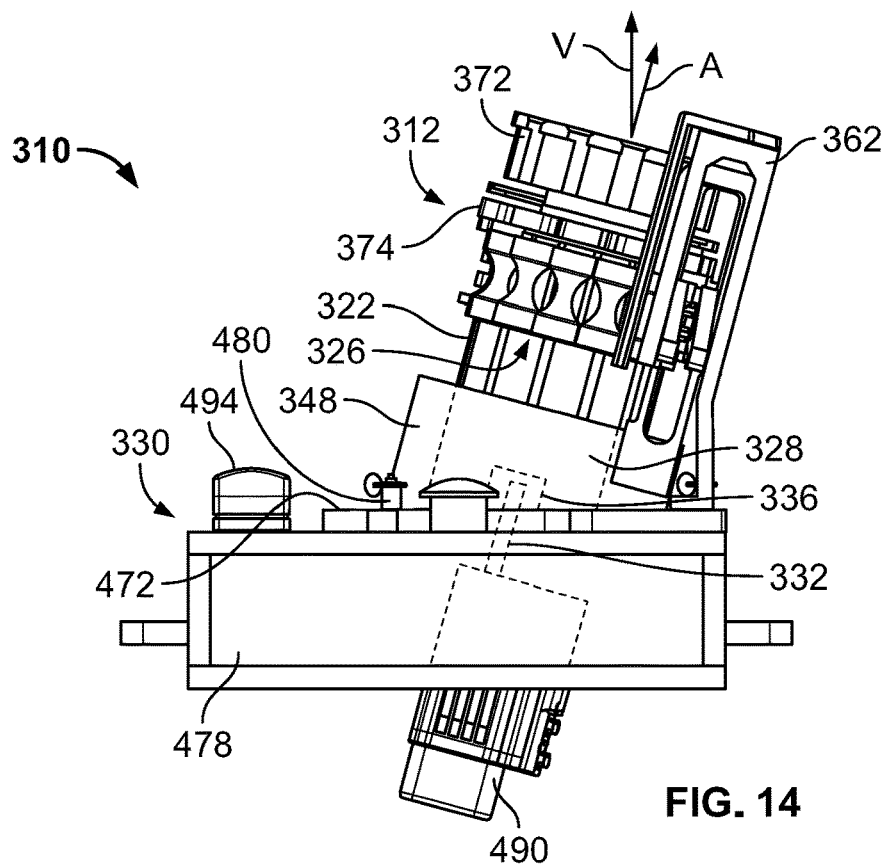
FIG. 14 is a side view of the third example plunger rod assembly system of FIG. 13.
Figure 15:
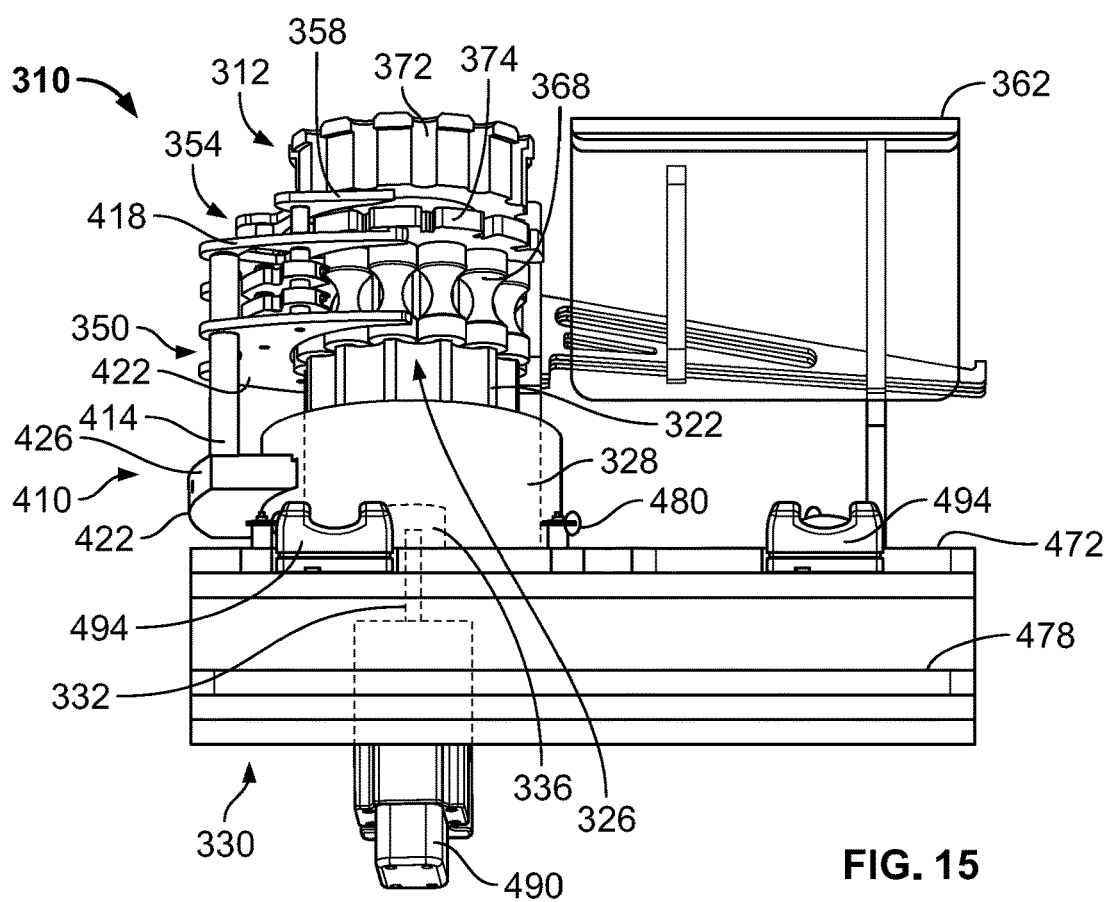
FIG. 15 is a front view of the third example plunger rod assembly system of FIG. 13.

A plunger rod assembly system for coupling a plunger rod to a prefilled syringe assembly is illustrated and described herein. FIGS. 1-4 illustrate a first example plunger rod assembly machine 10 depicted in various stages of coupling a plunger rod 14 and a prefilled syringe assembly 18. FIGS. 5-10 illustrate various components of the machine 10 in more detail, and FIGS. 11 and 12 illustrate an adaptive system to convert the non-automated machine 10 of FIGS. 1-4 to a second example plunger rod assembly system that is semi-automated. A third example plunger rod assembly system is illustrated in FIGS. 13-15 and may incorporate any or all of the various components of the previous illustrations to couple a plunger rod 14 to a syringe assembly 18. The term "syringe assembly" 18 may refer to a prefilled syringe or an empty syringe.

Figure 1:
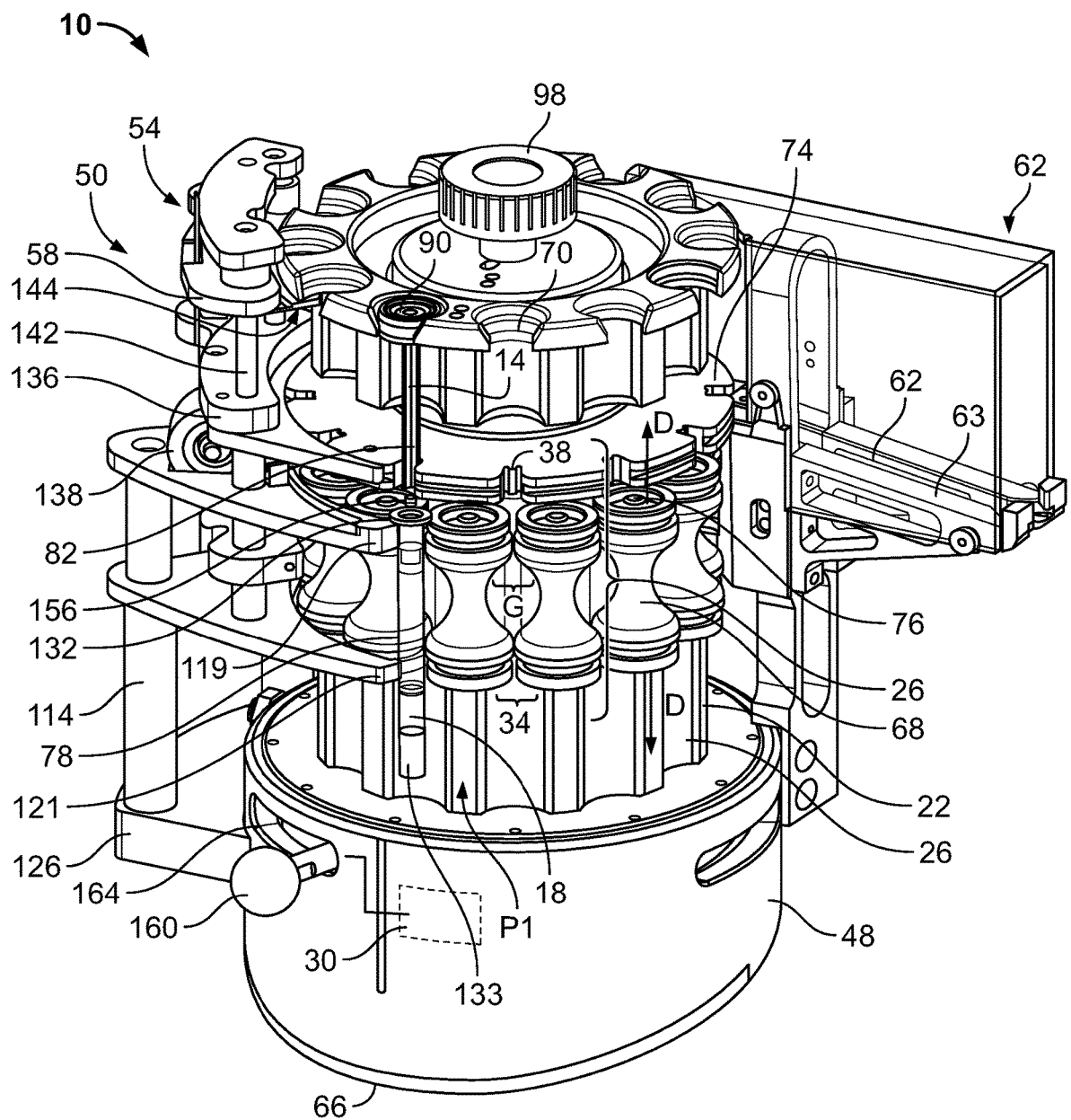
FIG. 1 is a front perspective view of a first example plunger rod assembly machine with a plunger rod and syringe assembly positioned thereon in accordance with teachings of the present disclosure.

In FIG. 1, the first example of a plunger rod assembly system 10 for coupling a plunger rod 14 to a syringe assembly 18 is illustrated. The plunger rod assembly system 10 is a machine having a carriage 22 with a movable cradle 26 and an actuating device 30 operatively coupled to the carriage 22 and adapted to move the cradle 26 from a first position to a second position. The cradle 26 includes a seat portion 34 sized to receive the syringe assembly 18 and an aperture portion 38 disposed above the seat portion 34 and sized to receive the plunger rod 14. Depicted in the illustrated example, the carriage 22 is a rotating carousel with a plurality of cradles 26 carried by the carriage 22 and disposed about the perimeter of the carousel 22. For ease of reference, a single cradle 26 will be described as the carriage 22 rotates the cradle 26 between the first position and the second position. A "loaded cradle" 26 as used herein refers to the cradle 26 having the plunger rod 14 and syringe assembly 18 positioned thereon. While the machine 10 provides multiple cradles 26 in various positions, a "first position" P1 (seen in FIG. 1) refers to the position where the plunger rod 14 and syringe assembly 18 are positioned onto the cradle 26 but are not yet coupled to each other. A "second position" P2 (seen in FIG. 3) refers to any position of the loaded cradle 26 once the plunger rod 14 is coupled to the syringe assembly 18. As used herein, a "coupled plunger rod syringe assembly" 46 refers to a final product where the plunger rod 14 is coupled to the syringe assembly 18. The plunger rod 14 and the syringe assembly 18 may be loosely attached, removably secured to, or suitably fit onto the cradle 26.

Figure 2:
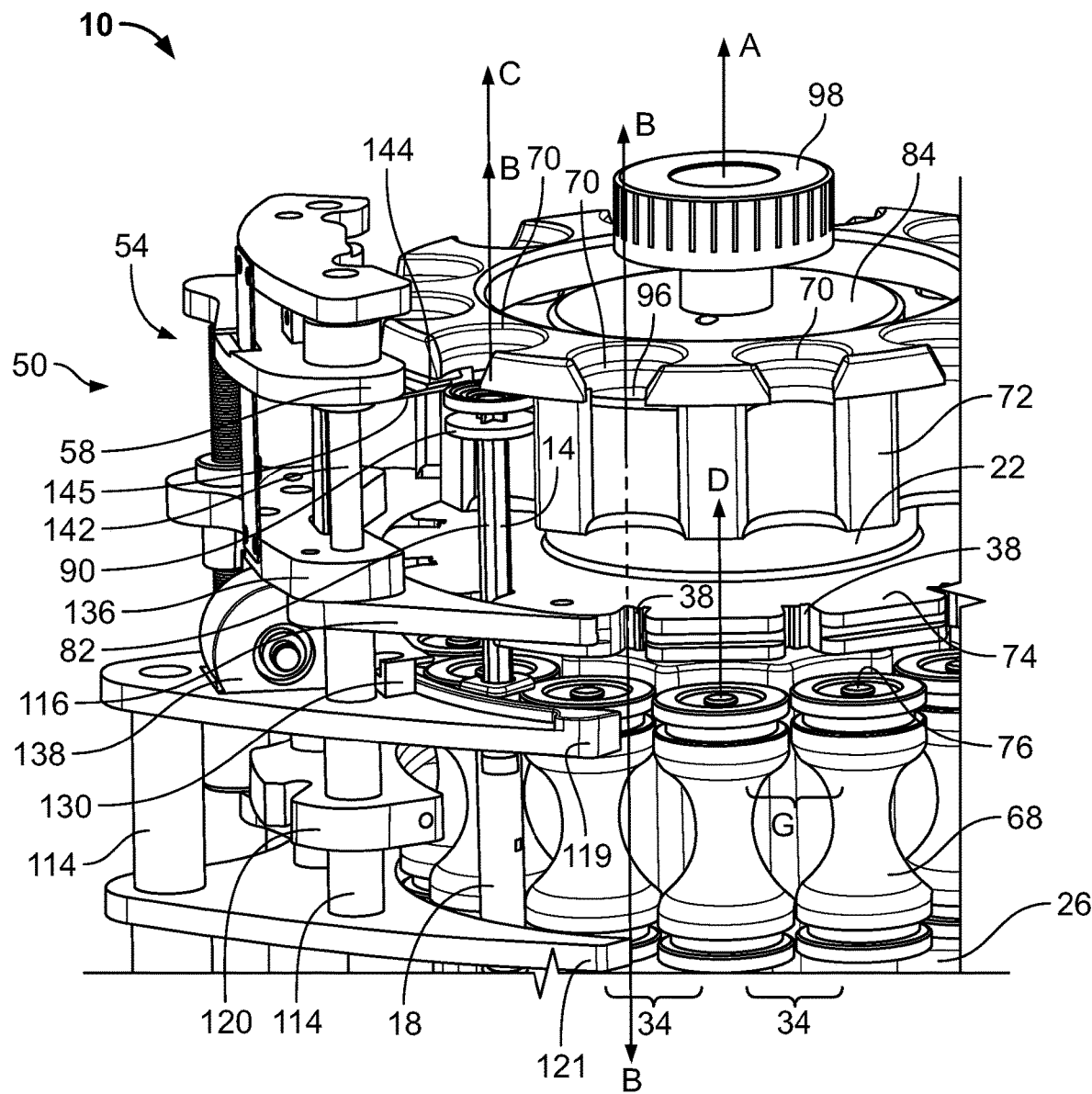
FIG. 2 is a partial front perspective view of the first example plunger rod assembly machine of FIG. 1 with the plunger rod and syringe assembly in an intermediate arrangement.
Figure 3:
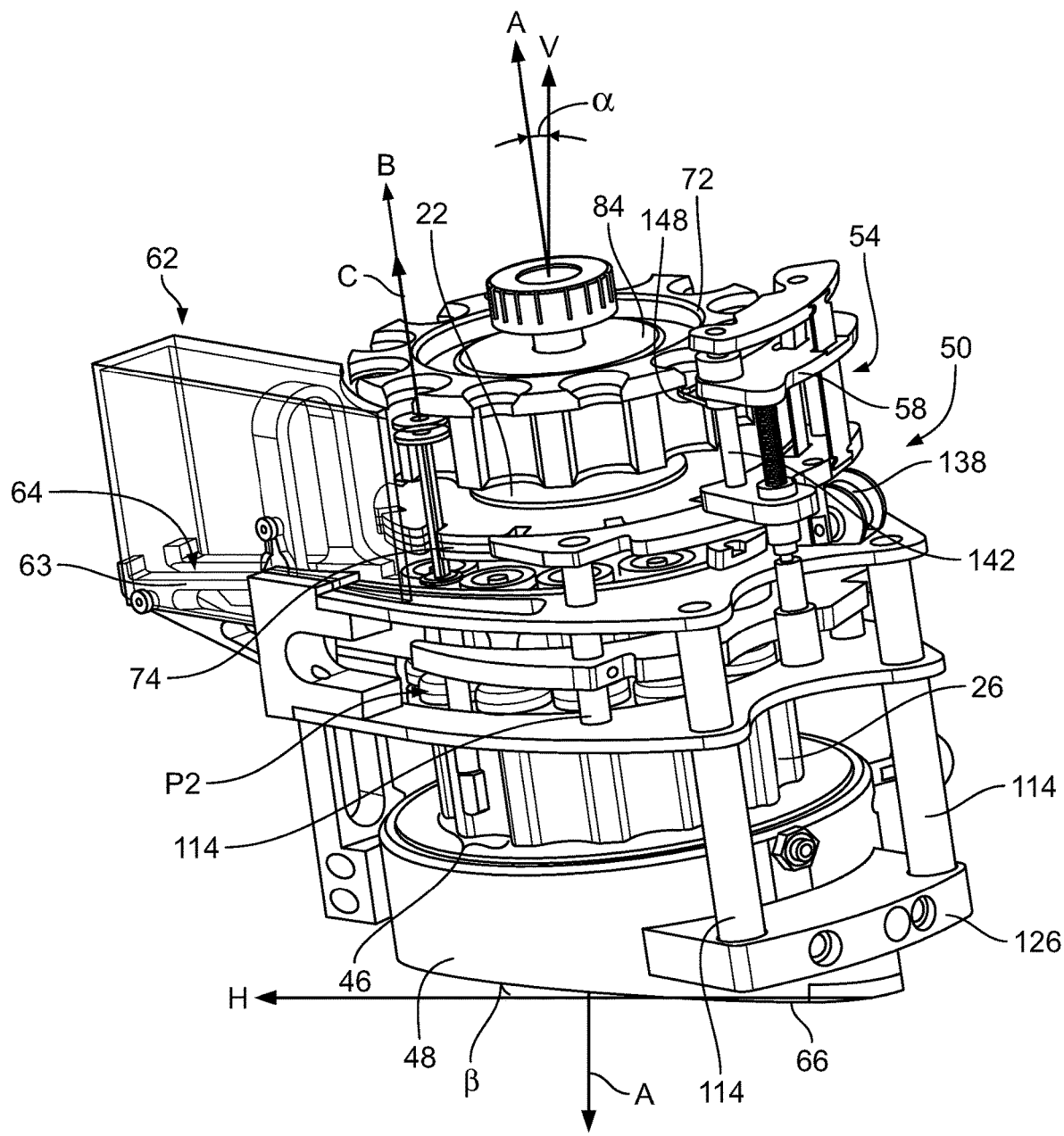
FIG. 3 is a back perspective view of the first example plunger rod assembly machine of FIG. 1 with the plunger rod and the syringe assembly in a coupled arrangement.
Figure 4:
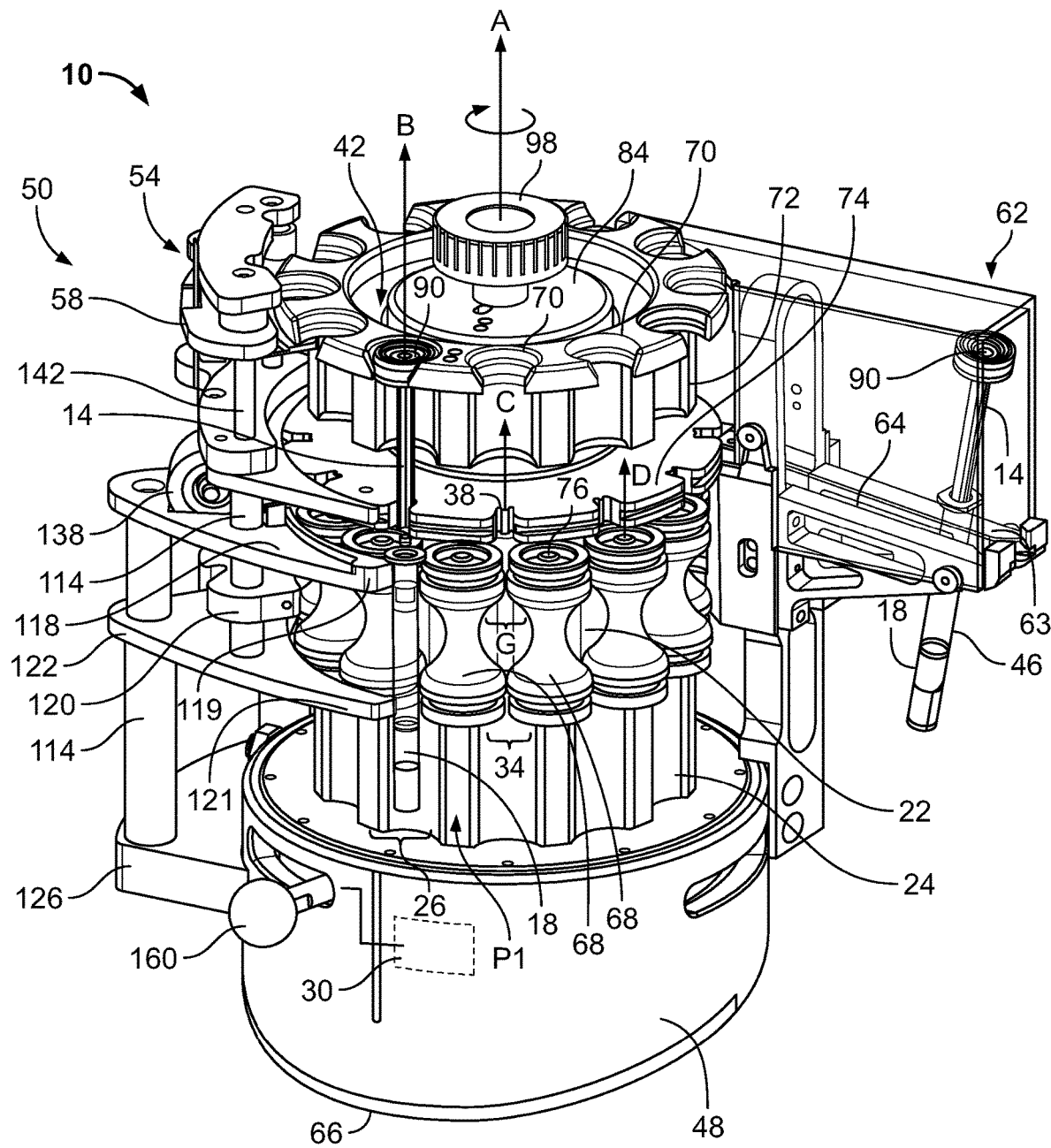
FIG. 4 is a front perspective of the first example plunger rod assembly machine of FIG. 1 with a first plunger rod and syringe assembly in a decoupled arrangement and a second plunger rod and syringe assembly in a coupled arrangement.

The function and operation of the machine 10 will be described when the cradle 26 is in three sequential positions: the first position P1, a position between the first position P1 and a second position P2, and the second position P2. The machine 10 is configured to couple the plunger rod 14 and the prefilled syringe assembly 18 by moving the cradle 26 from the first position P1 shown in FIG. 1, through an intermediate position shown in FIG. 2, and finally the second position P2 shown in FIG. 3 where the plunger rod 14 is coupled to the syringe assembly 18. The actuating device 30 disposed within a base 48 of the machine 10 drives the rotation of the carriage 22 and the loaded cradle 26 about a rotational axis A of the carriage 22. As the carriage 22 rotates, the loaded cradle 26 passes a guide assembly 50 attached to the base 48. The guide assembly 50 includes a pre-force plunger unit 54 which is configured to apply a constant downward force to the plunger rod 14 as the plunger rod 14 engages a pressure plate 58. Simultaneously, a friction element 60 (FIG. 9) of the guide assembly 50 engages and applies a rotational force (e.g., a torque) to the syringe assembly 18 to spin the syringe assembly 18 relative to the plunger rod 14 as the loaded cradle 26 passes under the pressure plate 58. The combination of the downward force applied by the pressure plate 58 and the rotational force applied by the friction element 60 effectively couples the plunger rod 14 to the syringe assembly 18 by the time the loaded cradle 26 reaches the second position P2. In FIG. 3, the coupled plunger rod syringe assembly 46 is in the second position P2 adjacent to an exit chute 62 that receives the coupled plunger rod syringe assembly 46. The cradle 26 is configured to release the coupled plunger rod syringe assembly 46 when the carriage 22 rotates again, and the cradle 26 is configured to deposit the coupled plunger rod syringe assembly 46 into the exit chute 62 as shown in FIG. 4. The carriage 22 described herein may be controlled or operated by a rotary actuator, but other embodiments may include a linear actuator. For example, the carriage 22 may be replaced with a linear assembly line, such as a conveyor belt, where the cradle 26 is indexed linearly. The carriage 22 may include one or more movable cradles 26 that are coupled to a linear drive mechanism that moves the cradles 26 linearly. In this example, the guide assembly 50 may be positioned relative to the linear conveyor belt or other method of linear conveyance to interact with the movable cradles 26 to couple the plunger rod 14 to the syringe assembly 18.

As shown in FIGS. 1, 3, and 4, the machine 10 is oriented at an angle when the base 48 of the machine 10 sits on a flat surface. As seen in FIG. 3, the rotational axis A of the carriage 22 is disposed at an angle α relative to vertical V, and a bottom surface 66 of the base 48 is disposed at angle β relative to horizontal H. The rotational and/or longitudinal axis A of the carriage 22 is also parallel to a cradle axis B that is coaxial with longitudinal axes C of the plunger rod 14 and syringe assembly 18 when the plunger rod 14 and syringe assembly 18 are disposed in the cradle 26. The cradle axis B and the rotational axis A are disposed at the angle α that is greater than zero degrees relative to vertical V. In one version, the angle α can be between 1 degree and 10 degrees, between 5 degrees and 10 degrees, between 5 degrees and 15 degrees, between 5 degrees and 20 degrees, between 5 degrees and 30 degrees, or any other suitable angle.

As mentioned earlier, the term "cradle" 26 refers to the structure that receives the plunger rod 14 and syringe assembly 18. Each cradle 26 includes a seat portion 34 defined by a pair of rollers 68, an orifice 70 of a plunger rod locating base 72, and the aperture portion 38 defined by a plunger rod grip disk 74. The rollers 68, the plunger rod locating base 72, and the plunger rod grip disk 74 are attached to the carriage 22 and are rotatable about the rotational axis A when the carriage 22 is actuated by the actuating device 30. The locating base 72 includes a plurality of evenly spaced orifices 70 and the plunger rod grip disk 74 includes a plurality of evenly spaced apertures 38. The locating base 72 and the grip disk 74 are spaced apart and positioned relative to the rollers 68 so that each cradle 26 is defined by one orifice 70, one aperture 38, and one seat portion 34 that are coaxial and arranged to receive a plunger rod 14 aligned with a syringe assembly 18. Each roller 68 is rotatable about a pin 76 disposed through a central axis D of the roller 68, and each pin 76 is secured to a bottom portion 24 of the carriage 22. Each roller 68 is spaced away from an adjacent roller 68 a predetermined distance defining a gap G so that a syringe barrel 78 may fit within the seat portion 34 between and in engagement with two adjacent rollers 68. First and second adjacent rollers 68 of the seat portion 34 are adapted to engage the syringe barrel 78 of the syringe assembly 18 and retain the syringe barrel 78 in the gap G when carried by the cradle 26.

The rollers 68 are arranged to loosely hold the syringe barrel 78 of the syringe assembly 18 when the syringe assembly 18 is attached to, or otherwise disposed on, the machine 10 in the first position P1, and to release the syringe barrel 78 when the cradle 26 moves toward the exit chute 62. In the disclosed versions, the angled orientation of the carriage 22 enables the cradle 26 to hold the syringe barrel 78 while the cradle 26 moves from the first position P1 toward the second position P2. Additionally, the angled orientation of the machine 10 permits the cradle 26 to release the coupled plunger rod syringe assembly 46 into the exit chute 62 after the cradle 26 passes the second position P2. When the carriage 22 rotates again, the coupled plunger rod syringe assembly 46 is received by a slot 64 of the exit chute 62 and the coupled plunger rod syringe assembly 46 may slide down a ramp 63 where the coupled plunger rod syringe assembly 46 remains until removed. The slot 64 is sized to receive a particular size syringe assembly 18 so that the coupled plunger rod and syringe assembly 46 can easily slide down the ramp 63 for storage in the exit chute 62. The ramp 63 may be sized and angled to hold a batch of coupled plunger rod syringe assemblies 46.

The dimensions of the cradle 26 are based on the requirements of the syringe assembly 18 and plunger rod 14. In particular, the seat portion 34 is sized to receive a specific type/size of syringe assembly 18 and the aperture portion 38 and orifice 70 of the cradle 26 are also sized to receive a specific type/shape of plunger rod 14. In the illustrated example, the machine 10 is specifically designed to couple a plunger rod 14 and syringe assembly 18 of a particular size. In other embodiments, the machine 10 may be adjusted to accommodate different sizes of plunger rods 14 and syringe assemblies 18. The machine 10 may be designed to accommodate one syringe assembly size, for example a 2.25 mL glass syringe assembly 18. As such, the spacing between two adjacent rollers 68 is arranged so that the syringe assembly 18 having a 2.25 mL syringe barrel 78 may be loosely attached to the cradle 26. Each aperture 38 of plunger rod grip disk 74 is designed to accommodate a particular shape of a plunger rod body 82 used with a 2.25 mL syringe assembly 18. For a plunger rod 14 with an X-shaped cross-section, the aperture portion 38 may include a plurality of ridges to receive the plunger rod body 82 and to limit rotational, angular, and lateral movement of the plunger rod 14 relative to the axis C when the loaded cradle 26 moves from the first position P1 to the second position P2. The rollers 68, on the other hand, are freely rotatable about the axis D and permit the syringe barrel 78 to rotate about the axis B of the cradle 26 when the friction element 60 contacts the syringe barrel 78, as will be described in further detail below. The rollers 68, the plunger rod grip disk 74, and the plunger rod locating base 72 may be positioned to accommodate a specific height of a plunger rod body 82.

The machine 10 is configured to accommodate a variety of different fill levels of a particular size syringe assembly 18 by interchangeable plunger rod locating bases 72 and 86. Depicted in FIGS. 5-8, the plunger rod locating base 72 is selected from separate and interchangeable first and second plunger rod locating bases 72 and 86. The first plunger rod locating base 72 includes the orifice 70 sized to receive a particular size proximal end 90 of a plunger rod 14 and the second plunger rod locating base 86 includes an orifice 104 sized to receive a different size proximal end 90 of a plunger rod 14. The first plunger rod locating base 72 and corresponding plunger rod holding cap 84 shown in FIGS. 5 and 7 may be interchanged with the different locating base 86 and associated holding cap 84 shown in FIGS. 6 and 8. The first and second plunger rod locating bases 72 and 86 may differ in height to accommodate different plunger rod heights, and they may have different orifice 70 and 104 sizes to accommodate two sizes of plunger rod proximal ends 90. In the illustrated embodiment, the orifices 70 of the first locating base 72 are smaller in radius than the orifices 104 of the second locating base 86. While not illustrated, the machine 10 may be configured to operate with any number of different plunger rod locating bases, and the machine 10 is not limited to the two embodiments described and illustrated herein.

Figure 5:
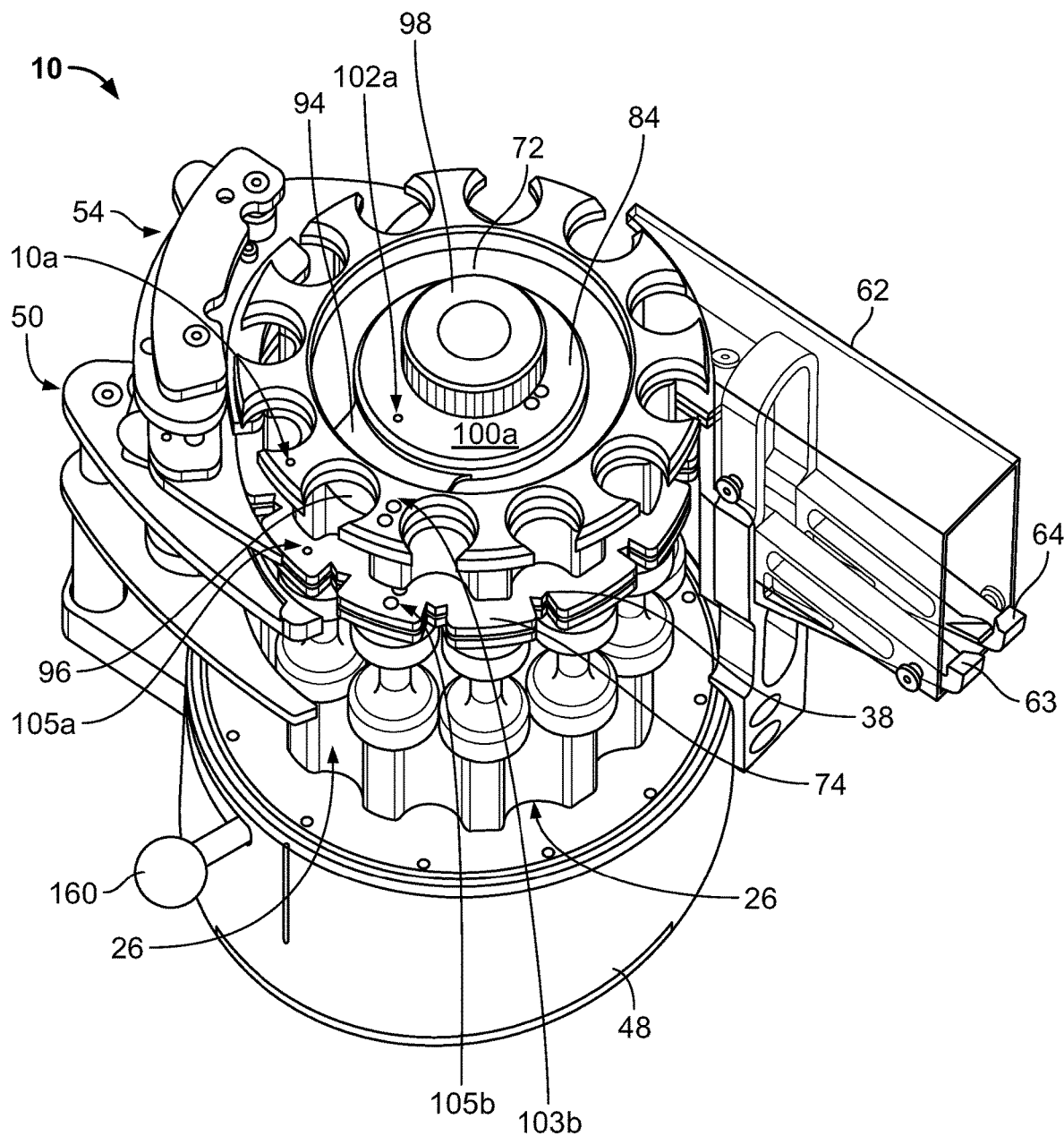
FIG. 5 is a top perspective view of the first example plunger rod assembly machine of FIG. 1, which illustrates a first example plunger rod locating base, a first example plunger rod holding cap, and a fastener.
Figure 6:
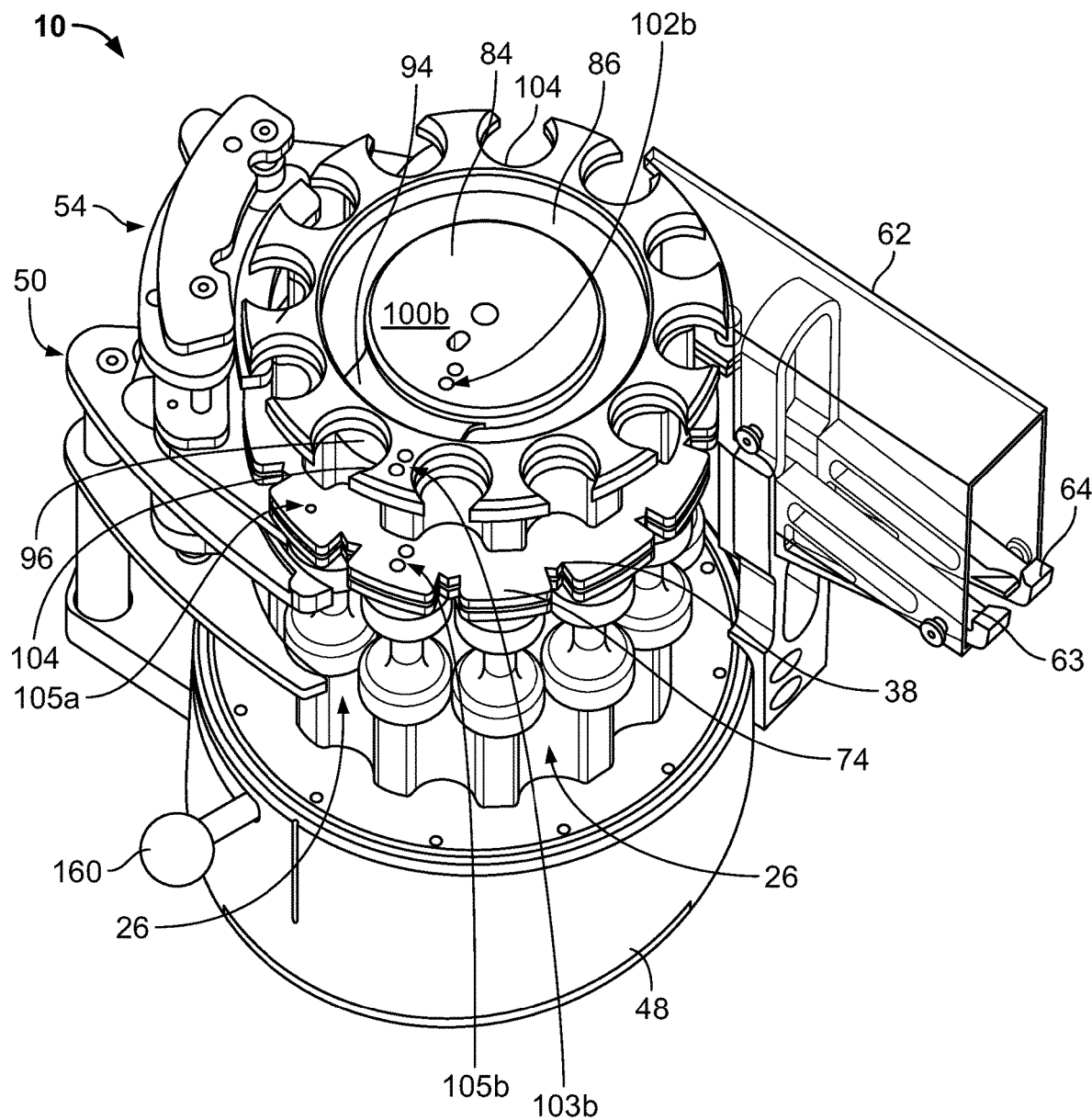
FIG. 6 is a top perspective view of the first example plunger rod assembly machine of FIG. 1 with a second example plunger rod locating base and a second plunger rod holding cap without the fastener.

Turning to FIGS. 5 and 6, the first plunger rod locating base 72 and holding cap 84 are removably attached to the machine 10. The first plunger rod locating base 72 is coupled to the carriage 22 and is disposed above the plunger rod grip disk 74 so that the orifices 70 placed about the perimeter of the locating base 72 are coaxial with the apertures 38 of the grip disk 74. Each orifice 70 is sized to receive a flanged proximal end 90 of the plunger rod 14 and provides sufficient clearance to permit the flanged proximal rod end 90 to fall through the orifice 70 when the cradle 26 moves from the first position P1 to the second position P2. The holding cap 84 is disposed on top of the locating base 72 and includes an outwardly extending tab 94 arranged to extend into the orifice 70 when the locating base 72 and holding cap 84 are attached to the machine 10. Both the holding cap 84 and the plunger rod locating base 72 are removably attached to the machine 10 via a threaded fastener 98. While the locating base 72 is movably coupled to the carriage 22 (such that the locating base 72 rotates with the carriage 22), the holding cap 84 and the threaded fastener 98 are fixed to the machine 10 and do not rotate with the carriage 22 about the axis A. The holding cap 84 provides a holding function to the plunger rod 14 when the plunger rod 14 is first positioned onto the cradle 26. As shown in FIGS. 1 and 2, the flanged proximal end 90 of the plunger rod 14 is received by the orifice 70 of the locating base 72 and sits against a portion 96 of the tab 94 that extends into the orifice 70. The portion 96 of the tab 94 disposed in the orifice 70 holds the plunger rod 14 in suspension above the syringe assembly 18 positioned on the seat portion 34. As the loaded cradle 26 moves from the first position P1, the locating base 72 rotates relative to the extending tab 94, and the orifice 70 of the cradle 26 moves away from the portion 96 to release the plunger rod 14 therefrom. The flanged proximal end 90 of the plunger rod 14 drops below the orifice 70 of the locating base 72 and a distal end 156 of the plunger rod 14 contacts a plunger 158 disposed in the syringe barrel 78, as shown in FIG. 2.

Figure 7:
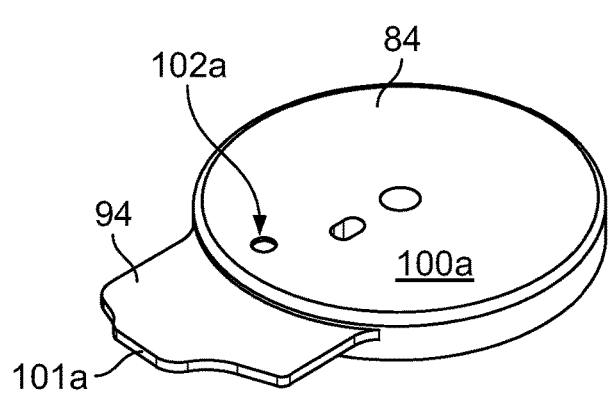
FIG. 7 is a top view of the first example plunger rod holding cap of FIG. 5.
Figure 8:
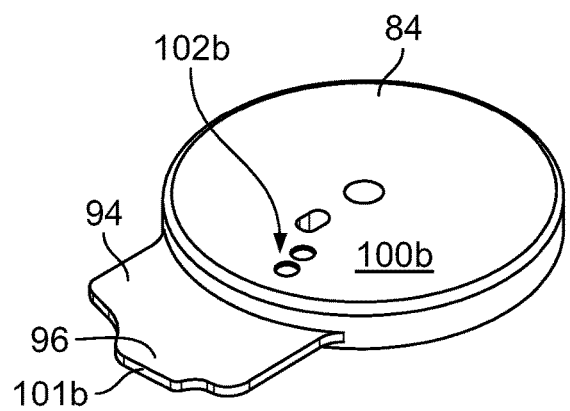
FIG. 8 is a top view of the second example plunger rod holding cap of FIG. 6.

FIG. 7 illustrates a first side 100a of the holding cap 84 associated with the first plunger rod locating base 72, and FIG. 8 illustrates a second side 100b of the holding cap 84 associated with the second plunger rod locating base 86. In each illustrated embodiment, the extending tab 94 of the holding cap 84 includes an asymmetrical contoured edge 101a and 101b which may be shaped according to variations in flanged ends 90 of different plunger rods 14. Each side 100*a* and 100*b* of the holding cap 84 includes a particular mark or markings 102*a* and 102*b* associated with corresponding markings 103*a* and 103*b* on the plunger rod locating base 72 and 86. The grip disk 74 also includes markings 105*a* and 105*b* that line up with the markings 102*a* and 102*b* to ensure alignment of the orifices 70 and 104 and the apertures 38 when assembling the cradles 26. As shown in FIG. 5, the markings 102*a*, 103*a*, and 105*a* may provide a visual indication that the plunger cap 84 is properly aligned with both the first plunger rod locating base 72 and the grip disk 74. To replace the first plunger rod locating base 72 with the second plunger rod locating base 86, a threaded fastener 98, which includes a hand operated knurled knob, is removed from the machine 10 and the holding cap 84 and the first locating base 72 are removed. The second locating base 86 is placed onto the carriage 22 so that the markings 103*b* align with the corresponding markings 105*b* on the grip disk 74. The holding cap 84 is flipped so that the second side 100*b* is facing away from the carriage 22 and then is placed on top of the second locating base 86 so that the markings 102*b* of the holding cap 84 align with the markings 103*b* of the second locating base 86 and the markings 105*b* of the grip disk 74. When properly assembled, the extending tab 94 is disposed within the orifice 104 of the cradle 26 in the first position P1. In the illustrated embodiments, the machine 10 includes the plunge rod holding cap 84 and plunger rod locating bases 72 and 86 for suspending the plunger rod 14 above the syringe assembly 18 when loaded to the cradle 26 in the first position P1. In a different embodiment, the plunger rod 14 and syringe assembly 18 may be loaded together such that the plunger rod 14 is not held by the holding cap 84 and locating base 72 and 86, and the distal end 156 may instead rest against the plunger 158 when the cradle 26 is in the first position P1. In this case, the locating base 72 and 86 and the holding cap 84 may be optionally attached to the machine 10 so that the cradle 26 is not defined by the orifice 70 and 104 of the locating base 72 and 86.

Figure 9:
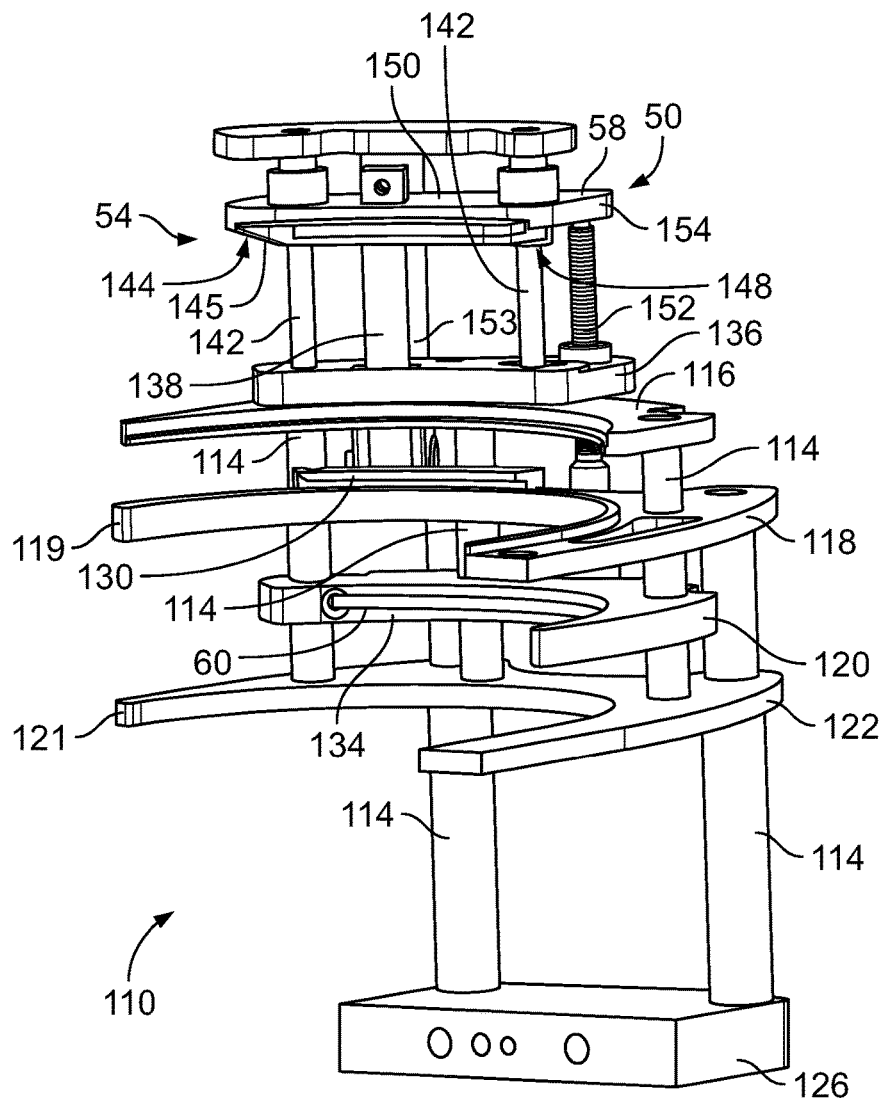
FIG. 9 is a perspective view of a guide assembly of the first example plunger rod assembly machine of FIG. 1, the guide assembly including a pre-force plunger unit.
Figure 10:
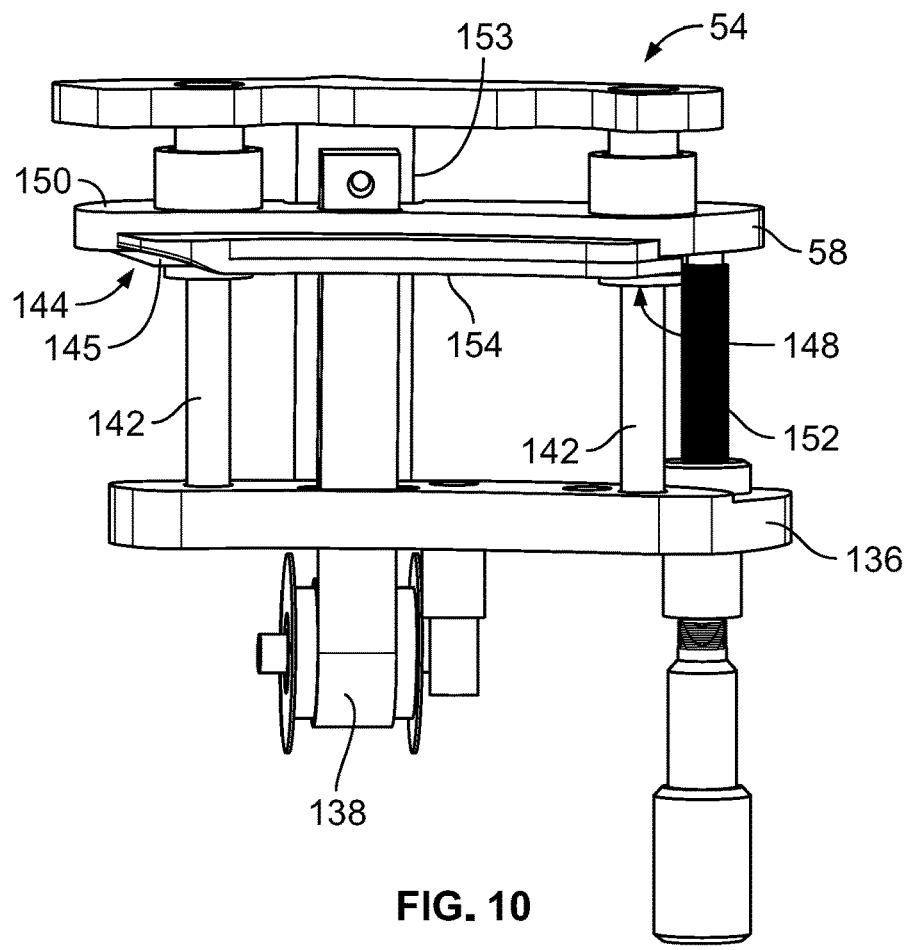
FIG. 10 is a perspective view of the pre-force plunger unit of the guide assembly of FIG. 9.

The guide assembly 50 in FIGS. 9 and 10 includes the pre-force plunger unit 54 of the machine 10 attached to an infeed guide assembly 110. The infeed guide assembly 110 includes a plurality of support rods 114 that connect a rod retaining guide 116, a top infeed guide 118, a guide plate 120, a bottom infeed guide 122, and a support base 126. Generally, the rod retaining guide 116, top infeed guide 118, guide plate 120, and bottom infeed guide 122 are contoured to partially surround and match the outer perimeter of the carriage 22. The support base 126 is attached to the base 48 of the machine 10 and the supporting rods 114 support the remaining elements of the infeed guide assembly 110 and the pre-force plunger unit 54. The top and bottom infeed guides 118 and 120 include cut-off ends 119 and 121, respectively, to receive and guide the loaded cradle 26 and prevent jamming while the carriage 22 rotates. A syringe barrel guide 130 attached to the top infeed guide 118 assists the infeed guides 118 and 120 by providing a barrier to a proximal end 132 of the syringe assembly 18 as the loaded cradle 26 moves passed the guide assembly 50 to the second position P2. As shown in FIG. 2, the syringe barrel guide 130 is an L-shaped bracket sized to receive and guide the proximal end 132 of the syringe assembly 18.

A friction element 60 is illustrated in FIG. 9 fixed to an interior edge surface 134 of the guide plate 120 and disposed adjacent to the carriage 22 and below the pressure plate 58. The friction element 60 is adapted to engage a syringe barrel 78 of the syringe assembly 18 attached to the cradle 26 when the cradle 26 moves from the first position P1 to the second position P2. The friction element 60 therefore applies a rotational force to the syringe barrel 78 to spin the syringe assembly 18 relative to the plunger rod 14. In the illustrated example, the friction element 60 is an elongated cord that extends along the interior edge surface 134 of the guide plate 120 so that the friction element 60 remains in contact with the syringe barrel 78 as the syringe assembly 18 moves along at least a portion of its path from the first position P1 to the second position P2. When the cradle 26 moves from the first position P1 to the second position P2, the syringe assembly 18 passes the guide assembly 50 and engages the friction element 60 protruding from the interior edge surface 134 of the guide plate 120. The friction element 60 contacts the syringe barrel 78 and causes the syringe barrel 78 and syringe assembly 18 to rotate about the longitudinal axis B of the cradle 26. So configured, as the cradle 26 carries the syringe assembly 18 in a first direction, the friction element 60 engages the syringe barrel 78 and applies a rotational force to the syringe barrel 78, causing the syringe barrel 78 to rotate between the rollers 68 of the cradle 26 in a direction opposite the first rotational direction of the carriage 22. Meanwhile, the plunger rod 14 disposed in the aperture portion 38 of the cradle 26 does not rotate relative to the cradle 26 or the syringe assembly 18, and instead receives a downward force from the pre-force plunger unit 54.

In a preferred example, the pressure plate 58 of the pre-force plunger unit 54 applies a constant force (e.g., approximately 2N in some versions) to the plunger rod 14, and the friction element 60 causes the syringe barrel 78 to rotate a maximum of four times to couple the plunger rod 14 and the syringe assembly 18. The length of the friction element 60 may be determined based on the mating relationship between the plunger 158 of the syringe assembly 18 and the plunger rod 14. For example, the plunger 158 may complete three rotations relative to the plunger rod 14 before the threaded distal end 156 of the plunger rod 14 adequately couples to the plunger 158. If the friction element 60 causes the syringe assembly 18 to rotate more than necessary, the excessive rotational force applied to the syringe assembly 18 may detrimentally effect the plunger 158, syringe barrel 78, or some other component of the syringe assembly 18. Thus, the length of the friction element 60 is based on a minimum number of rotations the syringe assembly 18 must take around the axis B to sufficiently couple the plunger 158 to the plunger rod 14 during a single index and without breaking. The friction element 60 may be an elastomeric material, such as silicon based rubber, gum rubber, latex, or other suitable material that would induce the syringe assembly 18 to spin relative to the cradle 26 when contacting the friction element 60. In another embodiment, the friction element 60 may be disposed on the rollers 68 rather than on the interior edge surface 134 of the guide plate 120. In this example, the guide plate 120 may be positioned so that a portion of the guide plate 120 contacts the friction element 60 disposed on the rollers 68, causing the rollers 68 to spin the syringe assembly 18 when the cradle 26 moves passed the guide assembly 50.

In FIGS. 9 and 10, the pre-force plunger unit 54 includes a base plate 136 attached to the rod retaining guide 116, the pressure plate 58, a constant tension spring 138 coupled to the pressure plate 58, and first and second guide posts 142. The elongated pressure plate 58 is positioned adjacent to the carriage 22 so that the cradle 26 moves beneath the pressure plate 58 when the cradle 26 moves from the first position P1 to the second position P2. In other words, the carriage 22 is rotationally disposed relative to the pressure plate 58. The pressure plate 58 is adapted to apply a downward force to the plunger rod 14 disposed in the aperture portion 38 of the cradle 26. In particular, the pressure plate 58 defines an inlet 144 (seen in FIG. 2) and an outlet 148 where the inlet 144 is sized to receive the proximal end 90 of the plunger rod 14 and apply a downward force onto the proximal rod end 90 of the plunger rod 14 as the plunger rod 14 moves from the inlet 144 to the outlet 148. The constant tension spring 138 is coupled to the pressure plate 58 and provides the downward force to the plunger rod 14 via the pressure plate 58 as the cradle 26 moves between the first position P1 and the second position P2. The pressure plate 58 is elongated with a ramped surface 145 at the inlet 144 to receive the proximal rod end 90 without colliding with the body 82 of the plunger rod 14.

The pressure plate 58 is slidably coupled to the first and second guide posts 142, enabling the pressure plate 58 to move along the posts 142 in a direction parallel to the rotational axis A. The guide posts 142 are disposed through first and second apertures of the pressure plate 58 and adjustably mount the pressure plate 58 relative to the carriage 22 such that the pressure plate 58 is adjustable to accommodate plunger rods 14 and plungers 158 disposed at different heights. The tension spring 138 is disposed through a third aperture of the pressure plate 58 and is fixed to the top surface 150 of the pressure plate 58 so that a constant force, e.g. 2 N, is always applied to the plunger rod 14. That is, as the plunger rod 14 moves from the first position P1 to the second position P2, the proximal rod end 90 of the plunger rod 14 exerts an upward force on the pressure plate 58 that may slightly lift the pressure plate 58. But the tension spring 138 ensures that a sufficient non-zero force is applied to the plunger rod 14 to positively influence coupling of the plunger rod 14 to the plunger 158. A threaded rod 152 is disposed through a bore in the base plate 136 and is adapted to engage a bottom surface 154 of the pressure plate 58 to adjust the height of the pressure plate 58 along the guide posts 142.

The pressure plate 58 may be adjusted to accommodate for different fill levels of the syringes assemblies 18, which correlate to the different positions of the plunger 158 within the syringe barrel 78. For example, it may be desirable to fill a syringe assembly 18 above the syringe assembly capacity marked by a fill line, causing the plunger 158 to be situated at position higher than the fill line at a distal end 133 of the syringe assembly 18. In another example, it may be desirable to fill the syringe assembly 18 below the syringe assembly capacity fill line, thereby causing the plunger 158 to be situated at a position lower than the fill line. To accommodate for a different fill level or plunger rod height, the position of the pressure plate 58 relative to the cradle 26 may be adjusted by rotating the threaded rod 152 in the clockwise direction or counterclockwise to raise or lower the pressure plate 58, respectively. A ruler 153 can be attached to the guide assembly 50 and remains stationary relative to the pressure plate 58 when the pressure plate 58 moves. The ruler 153 can be used to measure the distance the pressure plate 58 must be adjusted to accommodate for standard fill levels. For example, a syringe assembly 18 having a 1 mL volume capability may be filled to a fill level below or above a 1 mL fill line. The fill level determined by measured rulings on the syringe barrel 78 may indicate by how much the position of the pressure plate 58 may need to be adjusted outside the standard fill levels. The machine 10 and systems disclosed herein may be configured to operate with any number of different syringe assemblies 18, and are not limited to the 1 mL and 2.25 mL sizes described herein.

According to the present disclosure, the machine 10 is configured to index the cradle 26 to couple the plunger rod 14 to the syringe assembly 18. In a single indexed rotation, the distal end 156 of the plunger rod 14 can threadably couple to internal threads of the plunger 158 disposed in the proximal end 132 of the syringe assembly 18. For example, the loaded cradle 26 moves the plunger rod 14 to engage the pressure plate 58 while the friction element 60 engages the syringe barrel 78 to spin the syringe assembly 18. The combination of the downward force applied to the plunger rod 14 by the pressure plate 58 and the rotational force applied to the syringe assembly 18 induced by the friction element 60 permits the threaded distal end 156 of the plunger rod 14 to couple to the threaded surface of the plunger 158. In some versions, the machine may not include the pressure plate 58 at all and in such versions, coupling of the plunger rod 14 to the plunger 158 can be effected solely by the friction element 60 imparting a rotational force on the syringe barrel 78. In yet other versions, the machine 10 may not include a friction element 60 at all, and in those versions, coupling of the plunger rod 14 to the plunger 158 can be effected solely by applying a downward force to the plunger rod 14 with the pressure plate 58. In the latter configuration, the plunger rod 14 may not need to be threaded into the plunger 158, but rather simply friction fitted.

The machine 10 is arranged or programmed to index the cradle 26 such that the loaded cradle 26 moves between the first position P1 and the second position P2 in one movement of the carriage 22. The actuating device 30, which is operatively connected to the carriage 22, is adapted to index the cradle 26 so that the plunger rod 14 and syringe assembly 18 are coupled in less than three seconds. Each index of the cradle 26 may include rotating the carriage 22 approximately one third of a complete 360 degrees rotation, such as 120 degrees about the rotational axis A. For example, the cradle 26 in the first position P1 may be rotated about the axis A of the carriage 22 approximately 120 degrees relative to the first position P1 to reach the second position P2. Depending on the position of the guide assembly 50 and size of the carriage 22, the carriage 22 may be configured to index the cradle 26 in rotations less than 120 degrees about the axis A. In this way, the machine 10 limits instances of user-error or repetitive starting and stopping a continuously run machine. The machine 10 is configured to couple one plunger rod 14 to one syringe assembly 18 at a time.

The actuating device 30 may be arranged or programmed to index the cradle 26 via the carriage 22 only once upon an activation event. An activation event may be, for example, manually manipulating a lever 160 of the actuating device 30 or triggering a switch. One pull of the lever 160, for example, activates a servomotor or other mechanically-driven system of the actuating device 30 to index the cradle 26 between the first position P1 and the second position P2. The actuating device 30 may be further programmed so that the carriage 22 will not rotate until the lever 160 is pulled again or when some other activation event occurs. In other embodiments, the machine 10 may be actuated using another suitable mechanism other than the lever 160.

The lever 160 of the non-automated machine 10 illustrated in FIGS. 1-6 is operatively coupled to the carriage 22 and adapted to index the cradle 26 between the first position P1 and the second position P2. The lever 160 is movably attached to the base 48 and disposed within a slot 164. When the lever 160 is pulled from a resting position to a left-most end of the slot 164, the carriage 22 rotates until the lever 160 returns to its initial resting position in the slot 164. The lever 160 may be coupled to a mechanically-operated device or electrically-powered drive mechanism housed in the base 48 that converts the motion of the lever 160 to rotational motion of the carriage 22. In another embodiment, the actuating device 30 may be arranged or programmed to index the cradle 26 more than once upon the activation event. For example, the slot 164 of the lever 160 may be marked to indicate where the lever 160 can be pulled index the cradle 26 a certain number of times. For example, when the lever 160 is pulled to a first activated position, the cradle 26 indexes once; and when the lever 160 is pulled to a further second activated position along the slot 164, the cradle 26 indexes twice.

FIGS. 11 and 12 illustrate an adaptive system 170 to convert the non-automated machine 10 of FIGS. 1-6 into a semi-automated plunger rod assembly system 170. FIG. 11 illustrates the adaptive system 170 and FIG. 12 depicts the machine 10 of FIGS. 1-6 stationed on an actuating platform 172 of the adaptive system 170. The actuating platform 172 receives and secures the base 48 of the machine 10 to a table 178. A rigid member 182 is movably attached to the table 178 and extends vertically from the table 178 through a semi-circular bracket 186. The rigid member 182 carries the semi-circular bracket 186, which is adapted to smoothly glide on the surface of the table 178, when the rigid member 182 is actuated to move the lever 160. As shown in FIG. 12, the rigid member 182 is positioned adjacent to the lever 160 of the machine 10 when the lever 160 is in the resting or non-activated position. The semi-circular bracket 186 is shaped to match the contoured perimeter of the base 48. A servomotor 190 attached to the table 178 is operatively connected to the rigid member 182 via wiring disposed beneath the table 178. First and second two hand anti-tie down operation switches 194 are secured to opposite sides of the table 178 and are positioned to permit an operator to trigger the operation switches 194 simultaneously. The operation switches 194 are coupled to the servomotor 190 and are configured to trigger the servomotor 190 only when the switches 194 are pressed simultaneously. In operation, the servomotor 194 actuates the rigid member 182 to engage the lever 160 of the machine 10 and move the lever 160 within the slot 164. The rigid member 182 moves in an arc-shaped path to engage the lever 160 until the lever 160 reaches the left-most end of the slot 164. The servomotor 190 may be programmed to move the rigid member 182 only once when both operating switches 194 are triggered to index the cradle 26. In another embodiment, the servomotor 194 may be programmed to index more than once if desired. In this case, a control panel coupled to the activation switches 194 and the servomotor 190 may be configured to either index the cradle 26 more than once when a control panel switch is activated.

The adaptive system 170 of FIGS. 11 and 12 illustrates a plunger rod assembly system capable of converting the non-automated plunger rod assembly system 10 into a semi-automated system using the existing machine 10 of FIGS. 1-6. In the following FIGS. 13-15, a semi-automated plunger rod assembly system 310 is illustrated in accordance with another embodiment of the present disclosure. The plunger rod assembly system 310 is similar to the machine 10 described above, except that the system 310 is semi-automated and includes a different actuating device 330. Elements of the system 310 in FIGS. 13-15 which are similar to the elements of the machine 10 are designated by the same reference numeral, incremented by 300 or 400. For example, the system 310 includes an aperture portion 338, a ramp 363, a slot 364, rollers 368, orifices 370, a locating base 372, a plunger grip disk 374, support rods 414, a top infeed guide 418, and a support base 426. A description of many of these elements is abbreviated or even eliminated in the interest of brevity.

The plunger rod assembly system 310 of FIGS. 13-15 includes a machine 312 and exit chute 362 secured to a removable base plate 472. The base plate 472 is removably attached to a table 478 by a plurality of quick-change fasteners 480. An actuating device 330 is operatively coupled to a carriage 322 and adapted to index a cradle 326 carried by the carriage 322 from a first position P1 to a second position P2 to couple a plunger rod 14 to a syringe assembly 18. The plunger rod 14 and the syringe assembly 18 are not shown with the plunger rod assembly system 310, but may be positioned or attached to the machine 312 in the same or similar manner as described and illustrated in the previous figures. The actuating device 330 includes a servomotor 490 and first and second operation switches 494 for operatively controlling the servomotor 490. The servomotor 490, shown in FIGS. 14 and 15, is attached to the table 478 and positioned below the machine 312 so that the servomotor 490 can directly connect to the carriage 322.

To changeover to a different size syringe assembly 18, the carriage 322 may be selected from separate and interchangeable first and second carriages. The system 310 is configured to permit an operator to easily remove the selected carriage 322 and/or machine 312 from the servomotor 490, which is removably coupled or attached to the table 478, and replace the selected carriage 322 with a first carriage capable of receiving a different size syringe assembly 18. The first carriage 322 includes a cradle 326 having a seat portion 334 sized to receive a syringe assembly 18 of a first size, such as 1 mL syringe, and the second carriage includes a cradle having a seat portion sized to receive a syringe assembly of a second size, such as 2.25 mL syringe. The servomotor 490 of the actuating device 330 is adapted to couple to a base portion 328 of the first carriage 322 and a base portion of the second carriage. For example, the servomotor 490 may include a spline shaft 332 or other suitable device extending into a receiving member 336 disposed in the base portion 328 of the carriage 322. The receiving member 336 of both the first carriage 322 and the second carriage is adapted to couple with the spline shaft 332 of the servomotor 490 when the base 348 of the machine 312 is attached to the table 478. The machine 312 and exit chute 362 may be interchangeable with a second machine and second exit chute. Each machine 312 may include an attached guide assembly 350 and pre-force plunger unit 354 adapted to interact with the carriage 322 as described above in connection with the machine 10 of FIGS. 1-6.

For example, selected carriage 322 may be chosen by the operator based on the size of the syringe assembly 18 to be assembled. Each selected carriage 322 may correspond to a selected pressure plate 358, a selected friction element 360, and a selected guide plate 420. The first carriage 322 includes a first pressure plate 358 coupled to the carriage 322, and the second carriage includes a second pressure plate coupled to the second carriage. The first carriage 26 includes a first guide plate 420 coupled to the first carriage 322 and carrying a first friction element 360, and the second carriage includes a second guide plate coupled to the second carriage and carrying a second friction element. Accordingly, the selected pressure plate 358 is coupled to the selected carriage 322, and the selected friction element 360 is carried by a selected guide plate 420 coupled to the selected carriage 322.

According to a preferred method of using the plunger rod assembly system 10 and 310, the method may include positioning a syringe assembly 18 onto a cradle 26 and 326 of a carriage 22 and 322, where the cradle 26 and 326 of the carriage 22 and 322 is sized to receive a syringe assembly 18 of a specific size. The syringe assembly 18 includes a distal end 133 and a proximal end 132, a syringe barrel 78, and a plunger 158 disposed within the syringe barrel 78. A plunger rod 14 is positioned onto the cradle 26 and 326 of the carriage 22 and 322, where the plunger rod 14 includes a distal rod end 156 and a proximal rod end 90 where the distal rod end 156 is disposed above the proximal end 132 of the syringe assembly 18 and is axially aligned with the plunger 158. After both the plunger rod 14 and the first syringe assembly 18 are positioned onto the cradle 26 and 326, the method includes activating the actuating device 30 and 330 coupled to the carriage 22 and 322 to move the cradle 26 and 326 from a position P1 to a second position P2, thereby applying a force to the plunger rod 14 causing the plunger rod 14 to become coupled to the syringe assembly 18.

Activating the actuating device 30 and 330 includes rotating the carriage 22 and 322 so that the cradle 26 and 326 indexes from the first position P1 to the second position P2, where the syringe assembly 18 and the plunger rod 14 are positioned onto the cradle 26 and 326 in the first position P1 and the plunger rod 14 is coupled to the syringe assembly 18 in the second position P2. Further, the method includes rotating the carriage 22 and 322 about the axis A. When the cradle 26 and 326 is between the first and second positions P1 and P2, the method includes applying a downward force to the proximal rod end 90 of the plunger rod 14 when the cradle 26 and 326 moves from the first position P1 toward the second position P2. Applying a downward force to the proximal end 90 of the plunger rod 14 includes moving the plunger rod 14 beneath a pressure plate 58 and 358 positioned adjacent to the carriage 22 and 322 when the cradle 26 and 326 moves from the first position P1 to the second position P2. Further, the method includes applying a rotational force to a syringe barrel 78 of the syringe assembly 18 as the cradle 26 and 326 moves from the first position P1 to the second position P2. Applying the rotational force includes engaging the syringe assembly 18 with a friction element 60 and 360 disposed adjacent to the carriage 22 and 322 when the cradle 26 and 326 moves from the first position P1 and the second position P2. As the carriage 22 and 322 rotates in a first direction, rotating the syringe assembly 18 includes engaging the syringe barrel 78 with the friction element 60 and 360 and rotating the syringe assembly 18 in a direction opposite the first direction of rotation of the carriage 22 and 322.

To changeover the machine 10 and 312 in the second and third plunger rod assembly systems 170 and 310 of FIGS. 11-15, the method further includes decoupling a carriage, e.g. a second carriage, from the actuating device 30 and 330. If required, the method may include decoupling the second carriage from the table 478 by unlocking a plurality of quick-release or quick-change fasteners 480 to remove a second base plate from the table 478. Additionally, decoupling the second carriage from the actuating device 330 includes decoupling a spline shaft 332 of the servomotor 490 from a receiving member of the second carriage. Further, the method includes coupling the first carriage 22 and 322 to the actuating device 30 and 330 after decoupling the second carriage from the actuating device 30 and 330. Coupling the first carriage 22 and 322 to the actuating device 30 and 330 may include coupling the spline shaft 332 of the servomotor 490 to the receiving member 336 of the first carriage 22 and 322. The first carriage 22 and 322 includes a first movable cradle 26 and 326 adapted to receive a syringe assembly 18 of a first size. Additionally, the method may include fastening the first carriage 22 and 322 to the table 478 and/or base plate 472 by quick-change fasteners 480. The method further includes positioning a first syringe assembly 18 and a first plunger rod 14 onto the first movable cradle 26 and 326 of the first carriage 22 and 322. After both the first plunger rod 14 and the first syringe assembly 18 are positioned onto the cradle 26 and 326, the method includes activating the actuating device 30 and 330 coupled to the first carriage 22 and 322 to move the first cradle 26 and 326 from the first position P1 to the second position P2, thereby applying a force to the first plunger rod 14 causing the first plunger rod 14 to become coupled to the first syringe assembly 18. As recited above, the method includes applying a downward force to the proximal end 90 of the first plunger rod 14 and/or a rotational force to the syringe barrel 78 of the first syringe assembly when the first cradle 26 and 326 moves from the first position P1 to the second position P2. The method steps may be repeated to changeover the machine 10 and 312 to accommodate different sizes of syringe assemblies 18.

Prior to operating the plunger rod assembly system 10, 170, and 310, the actuating device 30 and 330 may be programmed to index the cradle 26 and 326 via the carriage 22 and 322 only once upon an activation event. Indexing the cradle 26 and 326 from the first position P1 to the second position P2 includes rotating the carriage 22 and 322 about the rotational axis A to couple the plunger rod 14 and the syringe assembly 18. Rotating the carriage 22 and 322 may include rotating the carriage 22 and 322 less than 120 degrees to move the cradle 26 and 326 from the first position P1 to the second position P2. When operating the first example machine 10, activating the actuating device 30 includes manually moving the lever 160 to rotate the carriage 22 and index the cradle 26 from the first position P1 to the second position P2. When operating the machine 10 with the adaptive actuating system 170 of FIGS. 11 and 12, activating the actuating device 30 includes triggering the operation switch 194 coupled to the servomotor 190 to slide the rigid member 182 and bracket 186 into engagement with the lever 160. When operating the third example system 310, activating the actuating device 330 includes triggering the operation switch 494 coupled to the servomotor 490 connected to the carriage 322.

In other embodiments, the machine 10 and 312 may be adapted to couple a plunger rod and a plunger of a syringe assembly according to the mating relationship of the plunger rod and the plunger. For example, the illustrated machines 10 and 312 are designed to couple the threaded distal end 156 the plunger rod 14 to the threaded surface of the plunger 158 by applying both a downward force to the plunger rod 14 and a rotational force to the syringe barrel 78. In another example, the plunger rod assembly system 10 and 310 may be adapted to couple a plunger rod 14 to a plunger 158 having a snap-fit mating relationship. In this example, each machine 10 and 312 may be configured to apply a downward force to the plunger rod 14 to sufficiently couple the plunger rod 14 and the plunger 158 without spinning the syringe assembly 18 relative to the cradle 26 and 326. The friction element 60 and 360 may be removed from the guide plate 120 and 420 so that the syringe assembly 18 does not rotate relative to the cradle 26 and 326 and the plunger rod 14.

The plunger rod assembly systems disclosed herein provide considerable benefits over current methods of automated plunger rod assembly systems. The non-automated and the semi-automated systems have a greatly reduced footprint compared to existing automated machines configured to assemble large batches. The disclosed system is an economical and efficient alternative over the existing automated machine. Typically, a small demand for plunger rod and syringe assemblies cannot justify the large capital investment for purchasing, operating, and maintaining expensive and complex automated machines designed to prepare large batches. However, the disclosed systems 10 and 310 are especially useful for assembling small batches of plunger rod syringe assemblies where access to fully automated machines is limited or unaffordable. Additionally, the disclosed systems are configured to index so that a plunger rod and syringe assembly are positioned onto the carriage and coupled before another plunger rod and syringe assembly are attached to, or positioned onto, the carriage. The indexing feature improves safety and reduces operator error because the systems are preconfigured to assemble plunger rod syringe assemblies without requiring the operator to know each step of the operating sequence or to interfere with the machinery between assembly steps. Additionally, the two hand anti-tie down operation switches ensure that the machine 10 and 312 cannot operate unless both hands of an operator trigger the switches. In other words, accidental operation or switching-on the machine would be greatly reduced if not completely prevented. The disclosed systems 10 and 310 are very simple to load, operate, and unload and do not require complex training, specialized education, or technical expertise to use the machinery. Both of these features of the disclosed systems may promote affordability and access to plunger rod syringe assembly technology.

The semi-automated systems greatly simply the operation of the assembly and process for adjusting and/or interchanging the components to assemble syringe assemblies of different sizes, materials, and fill levels. For example, the changeover process to adapt existing machines to assemble more than one size syringe assembly size is generally labor-intensive and requires disassembly, retooling, and re-assembly before operating the machine. In contrast, certain components of the disclosed plunger rod assembly systems can easily be replaced or adjusted within minutes and without requiring any additional tooling to changeover to assemble a syringe assembly of a different size. These features reduce costs of time and skilled labor and increase convenience and efficiency.

Drug Information

The above description describes various systems and methods for use with a plunger rod and syringe assembly system. It should be clear that the system, machine or methods can further comprise use of a medicament listed below with the caveat that the following list should neither be considered to be all inclusive nor limiting. The medicament will be contained in a reservoir of the syringe barrel of the syringe assembly. In some instances, the reservoir is a primary container that is either filled or pre-filled for treatment with the medicament. The primary container can be a pre-filled syringe.

For example, the syringe or syringe assembly may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RAN KL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT; 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AblA1; AbIF; Abl K, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid HCA (γ4), deposited at the ATCC under number PTA-5214, and a light chain encoded by a polynucleotide in plasmid 15H12/19D12 LCF (K), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP II/IIa receptor monoclonal antibody); Actemra® (anti-IL6 Receptor mAb); Avastin® (bevacizumab), HuMax-CD4 (zanolimumab); Rituxan®

(rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF-1R mAb; anti-IGF-1R mAb (HuMax-Inflam); anti-IL12 mAb (ABT-874); anti-IL12/1L23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCG8 mAb (MDX-1307); anti-mesothelin dsFv-PE38 conjugate (CAT-5001); anti-PD1mAb (MDX-1106 (ONO-4538)); anti-PDGFRa antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223, 593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

Although the plunger rod assembly systems, machine, methods, and elements thereof, have been described in terms of exemplary embodiments, they are not limited thereto. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent that would still fall within the scope of the claims defining the invention.

It should be understood that the legal scope of the invention is defined by the words of the claims set forth at the end of this patent. The appended claims should be construed broadly to include other variants and embodiments of same, which may be made by those skilled in the art without departing from the scope and range of equivalents of the systems, machines, methods, and their elements.

What is claimed:

1. A machine for coupling a plunger rod to a syringe assembly, the machine comprising:
    a selected carriage including a cradle having a seat portion sized to receive a syringe assembly and an aperture portion disposed above the seat portion and sized to receive the plunger rod;
    an actuating device operatively coupled to the selected carriage and adapted to move the cradle from a first position to a second position to couple the plunger rod to the syringe assembly; and
    wherein the selected carriage is selected from separate and interchangeable first and second carriages, wherein the first carriage includes a cradle adapted to receive a syringe assembly of a first size and the second carriage including a cradle sized to receive a syringe assembly of a second size that is different from the first size.

2. The machine of claim 1, further comprising a selected pressure plate positioned above the cradle so that the cradle moves beneath the selected pressure plate when the cradle moves from the first position to the second position, the selected pressure plate adapted to apply a downward force to the plunger rod disposed in the aperture portion of the cradle when the cradle moves from the first position to the second position.

3. The machine of claim 2, further comprising a selected constant tension spring operatively coupled to the selected pressure plate, the selected pressure plate defining an inlet portion adapted to receive a proximal end of the plunger rod when the cradle moves from the first position to the second position, the selected constant tension spring providing the downward force to the plunger rod, applied via the selected pressure plate, when the cradle moves between the first position and the second position.

4. The machine of claim 1, wherein the first carriage includes a first pressure plate coupled to the first carriage, and the second carriage includes a second pressure plate coupled to the second carriage, such that the selected pressure plate is coupled to the selected carriage.

5. The machine of claim 1, further comprising a quick-change fastener and a table, the selected carriage removably coupled to the table by the quick-change fastener.

6. The machine of claim 1, wherein the first carriage includes a first plunger rod base and the second carriage includes a second plunger rod base, and the actuating device includes a servomotor adapted to be operatively connected to the first and second bases.

7. The machine of claim 1, further comprising a selected friction element disposed adjacent to the selected carriage, the selected friction element adapted to engage a syringe barrel of the syringe assembly carried by the cradle as the cradle moves from the first position to the second position, the friction element adapted to apply a rotational force to the syringe barrel to spin the syringe assembly relative to the plunger rod when the cradle moves from the first position to the second position.

8. The machine of claim 7, wherein the first carriage includes a first guide plate coupled to the first carriage and carrying a first friction element and the second carriage includes a second guide plate coupled to the second carriage and carrying a second friction element such that the selected friction element is carried by a selected guide plate coupled to the selected carriage.

9. The machine of claim 1, further comprising a selected movable plunger rod base coupled to the selected carriage, the selected plunger rod base disposed above the cradle and including an orifice sized to receive a flanged proximal end of the plunger rod, the orifice coaxially aligned with the aperture portion of the cradle, the plunger rod base being movable with the cradle from the first position to the second position;
    a selected holding cap having an outwardly extending tab arranged to extend into the orifice of the selected plunger rod base, the selected holding cap removably attached to the selected plunger rod base; and
    wherein the selected holding cap is fixed relative to the selected carriage and is disposed in the orifice when the cradle is in the first position.

10. The machine of claim 9, wherein the selected plunger rod base is selected from separate and interchangeable first and second plunger rod bases, wherein the first plunger rod base includes an orifice adapted to receive a plunger rod of a first size and the second plunger rod base includes an orifice sized to receive a plunger rod of a second size that is different from the first size.

11. The machine of claim 1, wherein the cradle includes a cradle axis that is coaxial with longitudinal axes of the syringe assembly and the plunger rod when the syringe assembly and the plunger rod are disposed in the cradle, the cradle axis being disposed at an angle greater than zero degrees relative to vertical.

12. The machine of claim 11, wherein the selected carriage comprises a rotational carousel with a rotational axis that is parallel to the cradle axis such that the rotational axis of the selected carriage is disposed at an angle greater than zero degrees relative to vertical.

13. A machine for coupling a plunger rod to a syringe assembly, the machine comprising:
    a carriage having a movable cradle including a seat portion sized to receive a syringe assembly and an aperture portion disposed above the seat portion sized to receive a plunger rod;
    an actuating device operatively coupled to the carriage and adapted to move the cradle from a first position to a second position to couple the plunger rod to the syringe assembly;
    a pressure plate positioned adjacent to the carriage so that the cradle moves beneath the pressure plate when the cradle moves from the first position to the second position, the pressure plate adapted to apply a downward force to the plunger rod disposed in the aperture portion of the cradle when the cradle moves from the first position to the second position; and
    at least one of the following (a) through (e):
    (a) a constant tension spring operatively coupled to the pressure plate, the pressure plate defining an inlet portion adapted to receive a proximal end of the plunger rod when the cradle moves from the first position to the second position, the constant tension spring providing the downward force to the plunger rod, applied via the pressure plate, when the cradle moves between the first position and the second position;
    (b) a friction element disposed adjacent to the carriage and below the pressure plate, the friction element adapted to engage a syringe barrel of the syringe assembly carried by the cradle as the cradle moves from the first position to the second position, the friction element adapted to apply a rotational force to the syringe barrel to spin the syringe assembly relative to the plunger rod when the cradle moves from the first position to the second position;

(c) wherein the actuating device is operatively connected to the carriage and adapted to index the cradle between the first position and the second position in response to an activation event;

(d) wherein the cradle includes a cradle axis that is coaxial with longitudinal axes of the syringe assembly and plunger rod when the syringe assembly and plunger rod are disposed in the cradle, the cradle axis being disposed at an angle greater than zero degrees relative to vertical; and (e) wherein the carriage is selected from separate and interchangeable first and second carriages, the first carriage including a cradle having a seat portion sized to receive a syringe assembly of a first size and the second carriage including a cradle having a seat portion sized to receive a syringe assembly of a second size.

14. The machine of claim 13, further comprising a guide plate and the friction element fixed to the guide plate, wherein the friction element is an elongated cord of an elastomeric material.

15. The machine of claim 13, further comprising a movable plunger rod base coupled to the carriage, the plunger rod base disposed above the cradle and including an orifice sized to receive a flanged proximal end of the plunger rod, the orifice coaxially aligned with the aperture portion of the cradle, the plunger rod base being movable with the cradle from the first position to the second position;

a holding cap having an outwardly extending tab arranged to extend into the orifice of the plunger rod base, the holding cap removably attached to the plunger rod base; and wherein the holding cap is fixed relative to the carriage and is disposed in the orifice when the cradle is in the first position.

16. The machine of claim 15, wherein the plunger rod base is selected from separate and interchangeable first and second plunger rod bases, the first plunger rod base including an orifice sized to receive a flanged plunger rod end of a first size and the second plunger rod base sized to receive a flanged plunger rod end of a second size that is different from the first size.

* * * * *